United States Patent [19]

Gustin

[11] Patent Number: 5,545,556
[45] Date of Patent: Aug. 13, 1996

[54] MICROORGANISMS AND METHODS FOR THEIR USE

[75] Inventor: Michael C. Gustin, Houston, Tex.

[73] Assignee: William Marsh Rice University, Houston, Tex.

[21] Appl. No.: 32,382

[22] Filed: Mar. 18, 1993

Related U.S. Application Data

[63] Continuation-in-part of Ser. No. 704,943, May 23, 1991, abandoned.

[51] Int. Cl.⁶ .............................. C12P 21/06; C12N 1/20; C12N 15/00; C07H 19/00
[52] U.S. Cl. ..................... 435/254.2; 435/69.1; 435/193; 435/194; 435/252.3; 435/320.1; 435/254.21; 536/22.1; 536/23.1; 536/23.2
[58] Field of Search ................................. 435/69.1, 193, 435/194, 252.3, 255, 320.1; 536/22.1, 23.1, 23.2

[56] References Cited

PUBLICATIONS

Blomberg et al "Roles of glycerol . . . " J. Bact. 171:2 p. 1087–1092 Feb. 1989.
Glover *gene cloning* p1–20, 110–126.
Walter de Gruyter, *Concise Encyclopedia of Biochemistry*, (1983).
Parry J. M. et al., *Molec. Gen. Genet.*, 146: 27–35 (1976).
Walton E. F. et al., *Molec. Gen. Genet.*, 171: 111–114 (1979).
Johansson M. & Sjostrom J. E. *Biotechnol. Lett.*, 6: 49–54 (1984).

*Primary Examiner*—Robert A. Wax
*Assistant Examiner*—Hyosuk Kim
*Attorney, Agent, or Firm*—Baker & Botts, L.L.P.

[57] ABSTRACT

A novel group of mutant yeasts and novel methods for selecting and using the mutant microorganisms are set out. A novel process for using the mutant yeasts to produce fermentation products with a lower than usual glycerol content is also disclosed. Novel beverages, including beers, wines, ales, and sake, and novel low glycerol baked goods are also possible using the novel mutants of the invention. The mutant yeasts are of the genus Saccharomyces or genus Torulaspora. The mutants are also used to isolate DNA which can be inserted into yeasts to produce transformed yeasts having either greater or smaller glycerol production. The transformed yeasts may also be used to produce novel beverages, baked goods, or glycerol.

35 Claims, 13 Drawing Sheets

FIGURE 5

```
   1 ATCGATTGAAGGAAATAAGAGGAATAGCGCAAGTTGTTAGGAAAGCGTTCTTTATCTCCA   60
  61 AGACTTTGCCCTGTATATAATTAAACACCTCAAAGCGCTTCGTCATGGATGGAGATTATT  120
 121 CGGCATTTTGACATACAGGAGTGCCACATGCGAAAGCGGGAGTGGGCGTATTCTCTGGTT  180
 181 ACCCTACATGGTCTGGCGGCGTTATTATACGGGAGGATCTCGAAGGGAAGGAAGGAAAAA  240
 241 AAAAAAGAAAAGGCCAACGAAAAGCAAATATTATCTATCGTCGAAATTATCATACTATCT  300
 301 TACAATAAGAGTAGTAATTACTTTCTTGTTTGTATAGTGGAAGAGGAATTTGCGATAATA  360
 361 ATAGCAAAAGTAACTAATCTCTAACAAGAAACCTTATTTATTTTCTCTTTCTTCTATATT  420
 421 GGTAAATACTAGACTCGAAAAAAAGGAACAAAGGGAAAACAGGGAAAACTACAACTATCG  480
 481 TATATAATAATGACCACTAACGAGGAATTCATTAGGACACAGATATTCGGTACAGTTTTC  540
             M  T  T  N  E  E  F  I  R  T  Q  I  F  G  T  V  F
 541 GAGATCACAAATAGATACAATGATTTAAACCCCGTTGGGATGGGGCATTTGGGTTGGTT   600
      E  I  T  N  R  Y  N  D  L  N  P  V  G  M  G  A  F  G  L  V
 601 TGCTCAGCCACGGACACTTTGACATCTCAGCCAGTTGCCATTAAGAAAATCATGAAACCT  660
      C  S  A  T  D  L  T  S  Q  P  V  A  I  K  K  I  M  K  P
 661 TTTTCCACTGCAGTGCTGGCCAAAAGGACATATCGTGAACTAAAACTACTAAAACATCTA  720
      F  S  T  A  V  L  A  K  R  T  Y  R  E  L  K  L  L  K  H  L
 721 AGACACGAGAACTTGATTTGCCTTCAGGACATATTTCTTTCTCCATTGGAAGATATATAT  780
      R  H  E  N  L  I  C  L  Q  D  I  F  L  S  P  L  E  D  I  Y
 781 TTTGTCACGGAATTACAAGGAACAGATTTACATAGACTCTTGCAAACAAGACCCTTGGAA  840
      F  V  T  E  L  Q  G  T  D  L  H  R  L  L  Q  T  R  P  L  E
 841 AAGCAATTTGTTCAGTATTTCCTATACCAAATTCTAAGGGGTTTAAAATACGTTCACTCC  900
      K  Q  F  V  Q  Y  F  L  Y  Q  I  L  R  G  L  K  Y  V  H  S
 901 GCGGGCGTCATTCATAGAGATTTGAAACCGAGCAACATTCTGATTAATGAAAACTGTGAT  960
      A  G  V  I  H  R  D  L  K  P  S  N  I  L  I  N  E  N  C  D
 961 TTGAAGATTTGCGATTTCGGTCTAGCAAGAATTCAAGACCCTCAAATGACAGGCTATGTT 1020
      L  K  I  C  D  F  G  L  A  R  I  Q  D  P  Q  M  T  G  Y  V
1021 TCCACTAGATACTACAGGGCACCTGAAATCATGCTAACGTGGCAAAAATATGACGTCGAG 1080
      S  T  R  Y  Y  R  A  P  E  I  M  L  T  W  Q  K  Y  D  V  E
1081 GTCGACATTTGGTCCGCTGGTTGTATTTTTGCCGAAATGATTGAAGGTAAGCCTTTGTTC 1140
      V  D  I  W  S  A  G  C  I  F  A  E  M  I  E  G  K  P  L  F
1141 CCTGGGAAAGATCATGTTCACCAATTTTCGATCATCACTGACTTGTTGGGATCTCCGCCA 1200
      P  G  K  D  H  V  H  Q  F  S  I  I  T  D  L  L  G  S  P  P
1201 AAGGATGTGATAAATACTATTTGTTCCGAATAACTACTCTAAAATTTGTTACTTCGTTACCA 1260
      K  D  V  I  N  T  I  C  S  E  N  T  L  K  F  V  T  S  L  P
1261 CACAGAGATCCAATTCCATTTTCTGAAAGATTTAAAACAGTCGAACCTGATGCCGTAGAC 1320
      H  R  D  P  I  P  F  S  E  R  F  K  T  V  E  P  D  A  V  D
1321 CTTTTGGAAAAAATGCTGGTTTTTGATCCTAAGAAGAGAATCACTGCGGCGGATGCCTTG 1380
      L  L  E  K  M  L  V  F  D  P  K  K  R  I  T  A  A  D  A  L
1381 GCTCATCCTTATTCGGCTCCTTACCACGATCCAACGGATGAACCAGTAGCCGATGCCAAG 1440
      A  H  P  Y  S  A  P  Y  H  D  P  T  D  E  P  V  A  D  A  K
1441 TTCGATTGGCACTTTAATGACGCTGATCTGCCTGTCGATACCTGGCGTGTTATGATGTAC 1500
      F  D  W  H  F  N  D  A  D  L  P  V  D  T  W  R  V  M  M  Y
1501 TCAGAAATCCTAGACTTCCATAAGATTGGTGGCAGTGATGGACAGATTGATATATCTGCC 1560
      S  E  I  L  D  F  H  K  I  G  G  S  D  G  Q  I  D  I  S  A
1561 ACGTTTGATGACCAAGTTGCTGCAGCCACCGCTGCCGCGGCGCAGGCACAGGCTCAGGCT 1620
      T  F  D  D  Q  V  A  A  A  T  A  A  A  A  Q  A  Q  A
1621 CAGGCTCAAGTTCAGTTAAACATGGCTGCGCATTCGCATAATGGCGCTGGCACTACTGGA 1680
      Q  A  Q  V  Q  L  N  M  A  A  H  S  H  N  G  A  G  T  T  G
1681 AATGATCACTCAGATATAGCTGGTGGAAACAAAGGTCAGCGATCATGTAGCTGCAAATGA 1740
      N  D  H  S  D  I  A  G  G  N  K  G  Q  R  S  C  S  C  K  *
1741 CACCATTACGGACTACGGTAACCAGGCCATACAGTACGCTAATGAGTTCCAACAGTAAAC 1800
1801 GTGTTTTTTTAATGTCCCTAACCACTCATTCTTACTTCTTTTTGATGTTTCTTTTTTTTA 1860
1861 TGGTACTCATAAAAGTATTTACGTATATAGTTGTATAGAGGAAACAAAAAAAAAAAGATA 1920
1921 AAACTCAATTACAAAGTAAAGTGGACGTATTTCGATCATGATTTTTTTCTGTTTTAACCG 1980
1981 CATTGGATTTTCTTGTAAAACTGGAAGAAAAAGGAAACTAAAAAGTCAAGAAAGACCTTT 2040
2041 TTAAGACTCCAAGAACCGTCACTTATGGCGTATTGTTTGTTTATCAGCACTTCTATCTTC 2100
2101 GATAAAGGTTTGTCTGTCTTATATTGTTTACATTTCAAGTCTAATTCTGTGCTTTTACCG 2160
2161 AAGAGGAATTTTCATAAATACGGAGAAAATATAAAAAAAAAGTAAATACAGAAAATAGAA 2220
2221 CAGTTGAAGCAGAAAAAGAGAACTTGCTAAATAGCTGTCTCACCCAGACAAGCGTATACT 2280
2281 TACCACATTTAGTCTTTTGCAATCTCATTCTTGTTGAAGATAACTATTACATTCACGGAC 2340
2341 TGTGGCAGAAACTTCTCCTTAAGAAATTAGGAACTCATAAAAGGAATCAGCAGCTCTATG 2400
2401 TAATATCAAAATCTTTTCTATTTTTTGTATTTATGCTCTCATTCATTAATTCTAACGGAG 2460
2461 CTATTTATTATAAACAGTGAAGATATAAACCATATGTCTAATAGAACAAATTTCAAAAAG 2520
2521 TCTTCAATTTCGTGGATGTGGGAATGCATTTATTAAAAATAATGAATGGCAACATACGAC 2580
2581 ACCAAAATAGGAACACTTTCAGTACTATACAGAACTACGGATCC 2624
```

FIGURE 10

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 2624 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Saccharomyces cerevisiae ( x i ) SEQUENCE DESCRIPTION: SEQ ID NO:1:

```
ATCGATTGAA  GGAAATAAGA  GGAATAGCGC  AAGTTGTTAG  GAAAGCGTTC  TTTATCTCCA      60

AGACTTTGCC  CTGTATATAA  TTAAACACCT  CAAAGCGCTT  CGTCATGGAT  GGAGATTATT     120

CGGCATTTTG  ACATACAGGA  GTGCCACATG  CGAAAGCGGG  AGTGGGCGTA  TTCTCTGGTT     180

ACCCTACATG  GTCTGGCGGC  GTTATTATAC  GGGAGGATCT  CGAAGGGAAG  GAAGGAAAAA     240

AAAAAAGAAA  AGGCCAACGA  AAAGCAAATA  TTATCTATCG  TCGAAATTAT  CATACTATCT     300

TACAATAAGA  GTAGTAATTA  CTTTCTTGTT  TGTATAGTGG  AAGAGGAATT  TGCGATAATA     360

ATAGCAAAAG  TAACTAATCT  CTAACAAGAA  ACCTTATTTA  TTTTCTCTTT  CTTCTATATT     420
```

```
GGTAAATACT AGACTCGAAA AAAAGGAACA AAGGGAAAAC AGGGAAAACT ACAACTATCG    480

TATATAATAA TGACCACTAA CGAGGAATTC ATTAGGACAC AGATATTCGG TACAGTTTTC    540

GAGATCACAA ATAGATACAA TGATTTAAAC CCCGTTGGGA TGGGGGCATT TGGGTTGGTT    600

TGCTCAGCCA CGGACACTTT GACATCTCAG CCAGTTGCCA TTAAGAAAAT CATGAAACCT    660

TTTTCCACTG CAGTGCTGGC CAAAAGGACA TATCGTGAAC TAAAACTACT AAAACATCTA    720

AGACACGAGA ACTTGATTTG CCTTCAGGAC ATATTCTTT  CTCCATTGGA AGATATATAT    780

TTTGTCACGG AATTACAAGG AACAGATTTA CATAGACTCT TGCAAACAAG ACCCTTGGAA    840

AAGCAATTTG TTCAGTATTT CCTATACCAA ATTCTAAGGG GTTTAAAATA CGTTCACTCC    900

GCGGGCGTCA TTCATAGAGA TTTGAAACCG AGCAACATTC TGATTAATGA AAACTGTGAT    960

TTGAAGATTT GCGATTTCGG TCTAGCAAGA ATTCAAGACC CTCAAATGAC AGGCTATGTT   1020

TCCACTAGAT ACTACAGGGC ACCTGAAATC ATGCTAACGT GGCAAAAATA TGACGTCGAG   1080

GTCGACATTT GGTCCGCTGG TTGTATTTTT GCCGAAATGA TTGAAGGTAA GCCTTTGTTC   1140

CCTGGGAAAG ATCATGTTCA CCAATTTTCG ATCATCACTG ACTTGTTGGG ATCTCCGCCA   1200

AAGGATGTGA TAAATACTAT TTGTTCCGAA AATACTCTAA AATTTGTTAC TTCGTTACCA   1260

CACAGAGATC CAATTCCATT TTCTGAAAGA TTTAAACAG  TCGAACCTGA TGCCGTAGAC   1320

CTTTTGGAAA AAATGCTGGT TTTTGATCCT AAGAAGAGAA TCACTGCGGC GGATGCCTTG   1380

GCTCATCCTT ATTCGGCTCC TTACCACGAT CCAACGGATG AACCAGTAGC CGATGCCAAG   1440

TTCGATTGGC ACTTTAATGA CGCTGATCTG CCTGTCGATA CCTGGCGTGT TATGATGTAC   1500

TCAGAAATCC TAGACTTCCA TAAGATTGGT GGCAGTGATG GACAGATTGA TATATCTGCC   1560

ACGTTTGATG ACCAAGTTGC TGCAGCCACC GCTGCCGCGG CGCAGGCACA GGCTCAGGCT   1620

CAGGCTCAAG TTCAGTTAAA CATGGCTGCG CATTCGCATA ATGGCGCTGG CACTACTGGA   1680

AATGATCACT CAGATATAGC TGGTGGAAAC AAAGGTCAGC GATCATGTAG CTGCAAATGA   1740

CACCATTACG GACTACGGTA ACCAGGCCAT ACAGTACGCT AATGAGTTCC AACAGTAAAC   1800

GTGTTTTTTT AATGTCCCTA ACCACTCATT CTTACTTCTT TTTGATGTTT CTTTTTTTA   1860

TGGTACTCAT AAAAGTATTT ACGTATATAG TTGTATAGAG GAAACAAAAA AAAAAAGATA   1920

AAACTCAATT ACAAAGTAAA GTGGACGTAT TTCGATCATG ATTTTTTTCT GTTTTAACCG   1980

CATTGGATTT TCTTGTAAAA CTGGAAGAAA AAGGAAACTA AAAAGTCAAG AAAGACCTTT   2040

TTAAGACTCC AAGAACCGTC ACTTATGGCG TATTGTTTGT TTATCAGCAC TTCTATCTTC   2100

GATAAAGGTT TGTCTGTCTT ATATTGTTTA CATTTCAAGT CTAATTCTGT GCTTTTACCG   2160

AAGAGGAATT TTCATAAATA CGGAGAAAAT ATAAAAAAAA AGTAAATACA GAAAATAGAA   2220

CAGTTGAAGC AGAAAAAGAG AACTTGCTAA ATAGCTGTCT CACCCAGACA AGCGTATACT   2280

TACCACATTT AGTCTTTTGC AATCTCATTC TTGTTGAAGA TAACTATTAC ATTCACGGAC   2340

TGTGGCAGAA ACTTCTCCTT AAGAAATTAG GAACTCATAA AAGGAATCAG CAGCTCTATG   2400

TAATATCAAA ATCTTTTCTA TTTTTTGTAT TTATGCTCTC ATTCATTAAT TCTAACGGAG   2460

CTATTTATTA TAAACAGTGA AGATATAAAC CATATGTCTA ATAGAACAAA TTTCAAAAG   2520

TCTTCAATTT CGTGGATGTG GGAATGCATT TATTAAAAAT AATGAATGGC AACATACGAC   2580

ACCAAAATAG GAACACTTTC AGTACTATAC AGAACTACGG ATCC                   2624
```

( 2 ) INFORMATION FOR SEQ ID NO:2:

( i ) SEQUENCE CHARACTERISTICS:
        ( A ) LENGTH: 3170 base pairs
        ( B ) TYPE: nucleic acid -continued (C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Saccharomyces cerevisiae (xi) SEQUENCE DESCRIPTION: SEQ ID NO:2:

| | | | | | |
|---|---|---|---|---|---|
| CAGTCAGCTT | TTCCTTCATC | TTTTTCAGTC | TAATCTAAGG | AAGAAGAAAA | GCACTTCAAT | 60 |
| ACGAATAGCT | ACCAACGTAC | CCAGTTCACG | TTGAACAAGC | AATAGAAAAC | CAAAATAACA | 120 |
| CTGCCTGTCA | CTATTTCTGT | GCCGAAATGA | CCACCACTGC | CCAAGACAAT | TCTCCAAAGA | 180 |
| AGAGACAGCG | TATCATCAAT | TGTGTCACGC | AGCTGCCCTA | CAAAATCCAA | TTGGGAGAAA | 240 |
| GCAACGATGA | CTGGAAAATA | TCTGCTACTA | CAGGTAACAG | CGCATTATTT | TCCTCTCTAG | 300 |
| AATACCTTCA | ATTTGATTCT | ACCGAGTACG | AGCAACACGT | TGTTGGTTGG | ACCGGCGAAA | 360 |
| TAACAAGAAC | CGAACGCAAC | CTGTTTACTA | GAGAAGCGAA | AGAAAAACCA | CAGGATCTGG | 420 |
| ACGATGACCC | ACTATATTTA | ACAAAGAGC | AGATCAATGG | GTTGACTACT | ACTCTACAAG | 480 |
| ATCATATGAA | ATCTGATAAA | GAGGCAAAGA | CCGATACTAC | TCAAACAGCT | CCCGTTACCA | 540 |
| ATAACGTTCA | TCCCGTTTGG | CTACTTAGAA | AAAACCAGAG | TAGATGGAGA | AATTACGCGG | 600 |
| AAAAAGTAAT | TTGGCCAACC | TTCCACTACA | TCTTGAATCC | TTCAAATGAA | GGTGAACAAG | 660 |
| AAAAAAACTG | GTGGTACGAC | TACGTCAAGT | TTAACGAAGC | TTATGCACAA | AAATCGGGG | 720 |
| AAGTTTACAG | GAAGGGTGAC | ATCATCTGGA | TCCATGACTA | CTACCTACTG | TTATTGCCTC | 780 |
| AACTACTGAG | AATGAAATTT | AACGACGAAT | CTATCATTAT | TGGTTATTTC | CATCATGCCC | 840 |
| CATGGCCTAG | TAATGAATAT | TTTCGTTGTT | TGCCACGTAG | AAAACAAATC | TTAGATGGTC | 900 |
| TTGTTGGGGC | CAATAGAATT | TGTTTCCAAA | ATGAATCTTT | CTCCCGTCAT | TTTGTATCGA | 960 |
| GTTGTAAAAG | ATTACTCGAC | GCAACCGCCA | AAAAATCTAA | AAACTCTTCC | AATAGTGATC | 1020 |
| AATATCAAGT | CTCTGTGTAC | GGTGGTGACG | TACTCGTAGA | TTCTTTGCCT | ATAGGTGTTA | 1080 |
| ACACAACTCA | AATACTAAAA | GATGCTTTCA | CGAAGGATAT | AGATTCCAAG | GTTCTTTCCA | 1140 |
| TCAAGCAAGC | TTATCAAAAC | AAAAAAATTA | TTATTGGTAG | AGATCGTCTG | GATTCCGTCA | 1200 |
| GAGGCGTCGT | TCAAAAATTA | AGAGCTTTCG | AAACTTTCTT | GGCCATGTAT | CCAGAATGGC | 1260 |
| GAGATCAAGT | GGTATTGATC | CAAGTCAGCA | GTCCTACTGC | CAACAGAAAT | TCCCCCCAAA | 1320 |
| CTATCAGATT | GGAACAACAA | GTCAACGAGT | TGGTTAACTC | CATAAATTCT | GAATACGGTA | 1380 |
| ATTTGAATTT | TTCTCCCGTC | CAGCATTACT | ATATGAGAAT | CCCTAAAGAT | GTATACTTGT | 1440 |
| CCTTACTAAG | AGTTGCAGAC | TTATGTTTAA | TCACAAGTGT | TAGAGACGGT | ATGAATACCA | 1500 |
| CTGCTTTGGA | ATACGTCACT | GTCAAATCGC | ACATGTCGAA | CTTTTTATGC | TACGGAAATC | 1560 |
| CATTGATCTT | AAGTGAGTTT | TCTGGCTCTA | GTAACGTATT | GAAAGATGCC | ATTGTGGTTA | 1620 |
| ACCCATGGGA | TTCGGTGGCC | GTGGCTAAAT | CTATTAACAT | GGCTTTGAAA | TTGGACAAGG | 1680 |
| AAGAAAAGTC | CAATTTAGAA | TCAAAATTAT | GGAAAGAAGT | TCCTACAATT | CAAGATTGGA | 1740 |
| CTAATAAGTT | TTTGAGTTCA | TTAAAGGAAC | AGGCGTCATC | TAATGATGAT | ATGGAAAGGA | 1800 |
| AAATGACTCC | AGCACTTAAT | AGACCTGTTC | TTTTAGAAAA | TTACAAGCAG | GCTAAGCGTA | 1860 |
| GATTGTTCCT | TTTTGATTAC | GATGGTACTT | TGACCCCAAT | TGTCAAAGAC | CCAGCTGCAG | 1920 |
| CTATTCCATC | GGCAAGACTT | TATACAATTC | TACAAAAATT | ATGTGCTGAT | CCTCATAATC | 1980 |

-continued

| | | | | | | |
|---|---|---|---|---|---|---|
| AAATCTGGAT | TATTTCTGGT | CGTGACCAGA | AGTTTTTGAA | CAAGTGGTTA | GGCGGTAAAC | 2040 |
| TTCCTCAACT | GGGTCTAAGT | GCGGAGCATG | GATGTTTCAT | GAAAGATGTT | TCTTGCCAAG | 2100 |
| ATTGGGTCAA | TTTGACCGAA | AAAGTTGATA | TGTCTTGGCA | AGTACGCGTC | AATGAAGTGA | 2160 |
| TGGAAGAATT | TACCACAAGG | ACCCCAGGTT | CATTCATCGA | AAGAAAGAAA | GTCGCTCTAA | 2220 |
| CTTGGCATTA | TAGACGTACC | GTTCCAGAAT | TGGGTGAATT | CCACGCCAAA | GAACTGAAAG | 2280 |
| AAAAATTGTT | ATCATTTACT | GATGACTTTG | ATTTAGAGGT | CATGGATGGT | AAAGCAAACA | 2340 |
| TTGAAGTTCG | TCCAAGATTC | GTCAACAAAG | GTGAAATAGT | CAAGAGACTA | GTCTGGCATC | 2400 |
| AACATGGCAA | ACCACAGGAC | ATGTTGAAGG | GAATCAGTGA | AAAACTACCT | AAGGATGAAA | 2460 |
| TGCCTGATTT | TGTATTATGT | TTGGGTGATG | ACTTCACTGA | CGAAGACATG | TTTAGACAGT | 2520 |
| TGAATACCAT | TGAAACTTGT | TGGAAAGAAA | AATATCCTGA | CCAAAAAAAT | CAATGGGGCA | 2580 |
| ACTACGGATT | CTATCCTGTC | ACTGTGGGAT | CTGCATCCAA | GAAAACTGTC | GCAAAGGCTC | 2640 |
| ATTTAACCGA | TCCTCAGCAA | GTCCTGGAGA | CTTTAGGTTT | ACTTGTTGGT | GATGTCTCTC | 2700 |
| TCTTCCAAAG | TGCTGGTACG | GTCGACCTGG | ATTCCAGAGG | TCATGTCAAG | AATAGTGAGA | 2760 |
| GCAGTTTGAA | ATCAAAGCTA | GCATCTAAAG | CTTATGTTAT | GAAAGATCG | GCTTCTTACA | 2820 |
| CCGGCGCAAA | GGTTTGAAAC | ACCCTTTTA | ACGAAATGGT | TATGACTAGA | CAGACATCTT | 2880 |
| ACGTCTTACT | CCTTCATGCT | TTATTTTTT | CTTTGTATTG | TATTTGAACA | GTCAATATGT | 2940 |
| GGTGTTGCGA | CGAAGGCATA | TATATAATAG | TCTCAACCCA | CCATTTCGA | AGATTACAT | 3000 |
| ACACATTATA | TTTTTATAAA | CTTCCAATAT | GTAATAACTT | TATATGATAT | GTAACTTCTC | 3060 |
| ACTATTATCC | TTACTATTAA | ACGGTTTTA | ATAAATATCA | TTGTTCTTTG | TTTTATTAAT | 3120 |
| GAGAAAAAGA | AATTTAATAC | AATGTCCGGC | GGGAAGAAAA | AAAATCGATG | | 3170 |

MICROORGANISMS AND METHODS FOR THEIR USE

RELATED APPLICATIONS

This Application is a continuation-in-part of application Ser. No. 07/704,943 filed May 23, 1991, now abandoned.

FIELD OF THE INVENTION

This invention relates to yeasts used in fermentation or baking processes and, more particularly, relates to yeast fermentation processes in which it is desirable to recover and dry solids from fermentation products and wherein the yeast produces a lower than normal amount of glycerol. In another embodiment, the yeasts of the invention are used to identify genes regulating glycerol production, yielding novel DNA segments, plasmids, shuttle vectors, and transformed yeast cells. In yet another embodiment, the transformed yeast cells are used in fermentation processes to produce novel products or in commercial glycerol production. In another embodiment, a DNA segment encoding a protein required for normal levels of glycerol biosynthesis in yeast is mutated and re-introduced into a yeast strain, replacing the normal gene. This yeast strain, carrying the mutant gene and producing less glycerol, may be used in fermentation or baking processes and produce a fermentation product containing a lower yield of glycerol, a higher yield of ethanol, or a higher ethanol to glycerol ratio than control strains lacking these mutations.

PRIOR ART

Yeast fermentation to leaven bread and produce alcoholic beverages has been known for thousands of years. A wide variety of carbohydrate containing materials is useable as feed stocks for yeast fermentation processes. Almost any carbohydrate containing material is a potentially useful carbon source for yeast fermentation processes. Well known examples include fruits such as grapes, berries, and apples, and grains such as wheat, rye, barley, rice, and corn. Yeast strains particularly adapted for various industrial applications have been produced by known genetic selection, selection following mutagenic treatment, by crossbreeding, and by hybridization. Improvement of yeasts by various techniques is reviewed by Spencer and Spencer, *Ann. Rev. Microbiol.* 37:121 (1983). Mutant yeast strains selected to produce lower than normal amounts of fusel oils are disclosed in U.S. Pat. No. 4,374,859. Mutant yeast strains producing maltase with sucrose as a carbon source are disclosed in U.S. Pat. No. 4,395,490. Direct fermentation of D-xylose to ethanol by a yeast mutant is disclosed in U.S. Pat. Nos. 4,368,268 and 4,511,656. Other known mutant yeast strains include temperature sensitive actin mutants reported by Novick and Botstein, *Cell* 40:405 (1985), and various abnormal amino acid biosynthesis mutants and omnipotent translational suppressor mutants disclosed by McCusker and Haber, *Genetics* 119:317 (1988).

Many commercial yeast strains, particularly those adapted to grow in high alcohol concentrations as well as yeast strains selected for baking, produce significant quantities of glycerol, typically between 5 and 10 g/l. Selective hybridization of wine yeasts for higher glycerol production has been carried out. Eustace and Thornton, *Can. J. Microbiol.* 33:112 (1987).

In many conventional fermentation processes, solids from the spent "mash" (i.e., remaining feed stock materials) are recovered and dried for animal feed and other purposes. Due to its hygroscopic properties and relatively low vapor pressure, glycerol interferes with the drying of recovered solids increasing the costs and energy required for drying. Reduction of glycerol production by yeast may also enhance yields of other products of fermentation (such as ethanol) important in the manufacture of beer, wine, ale, sake, fuel alcohol, and distilled spirits. In baked goods, glycerol produced by yeasts influences flavor and texture. Therefore, the availability of low glycerol producing yeast mutants or high glycerol producing transformed yeasts is desirable to provide a wider selection of flavor and texture in the finished baked products. Reduction or elimination of glycerol production is desirable when a dry flavor is desired or when a particular texture or flavor is sought in baked goods. Higher glycerol production increases body in wines and imports a sweeter flavor in beverages or baked goods. When glycerol production is enhanced in transformed yeasts, glycerol may become a major fermentation product recoverable in commercial quantities. However, such low glycerol production strains and high glycerol producing transformed strains have not been previously available in the art.

Mutant strains showing osmotic sensitivity have been previously reported. See for example Singh and Sherman, *Genetics* 89:653 (1978). The gene OSM1 was found closely linked to the gene for iso-1-cytochrome C on chromosome X. Mutations of the OSM1 gene often mutate the iso-1-cytochrome C gene as well. Another osmotic sensitive strain was disclosed by Ball, et al., *Mol. Gen. Genet.* 205:326 (1986). In this osmotic sensitive strain a chorismatic mutase gene defect eliminated biosynthesis of the desired and important amino acids phenylalanine and tyrosine. Ball, et al. established the identity of the chorismatic mutase structural gene AR07, with a gene necessary for growth in hypertonic media, OSM2. The Ball, et al. mutants were due to changes in a gene located on chromosome XVI. Neither of these osmotically sensitive strains were shown to have lowered glycerol production.

Yeast strains with mutations in genes affecting glycerol production have not previously been available. Heretofore, it has not been possible to isolate deoxyribonucleic acid (DNA) segments which complement a High Osmolarity Glycerol gene mutant. These and other limitations and disadvantages of the prior art are overcome by the present invention, however, and an improved yeast strain having reduced glycerol production is provided. A method of isolating the genes which lower glycerol production when mutated is also provided. Additional copies of the isolated genes may also be introduced to transform yeast cells for higher glycerol production.

The High Osmolality Glycerol gene found in unmutated, wild-type yeast is identified as "HOG". Mutated genes are identified as "hog". In general upper case gene designations refer to unmutated or wild-type and lower case designations indicate a mutated gene.

The use of a modified DNA segment containing a yeast gene to create a stable inactivating mutation in that gene in a host yeast strain is a well-established technique. Briefly, this technique, called one-step gene disruption (Rothstein, *Meth. Enzym.* 101:228 (1989)), consists of modifying a cloned gene in vitro to introduce an inactivating mutation and a dominant selectable marker into the gene. This modified DNA is inserted into the chromosome of a host strain by transformation. A gene disruption in a transformed strain is verified by a gel-transfer hybridization (Sambrook, Fritsch, and Maniatis, *Molecular Cloning, A Laboratory Manual,* 2nd Edition, Cold Spring Harbor Laboratory Press, Cold Spring Harbor (1989)), using genomic DNA from the strain and a probe derived from the cloned gene. A successful gene disruption occurs when the chromosomal copy of the gene is replaced with the genetically marked and mutated form of the gene. Three types of modifications produce inactivating mutations in a gene: disruption of a gene by insertion of foreign DNA, deletion of DNA from a gene, and substitution of deoxyribonucleotides in the DNA sequence of the gene. Mutations will cause inactivation of the gene and the function of the protein it encodes when the mutations (a) alter non-coding DNA to inhibit the transcription of the DNA into messenger RNA or reduce the stability of the mRNA product or (b) alter protein-coding DNA to produce a non-functional protein product or no protein product. This strategy for creating yeast strains with inactivating mutations in specific genes has not previously been applied to creating yeast strains with a reduced biosynthesis of glycerol. The novel yeast strains and DNA segments of this invention are not disclosed or suggested in the prior art.

INVENTION SUMMARY

In this invention, novel yeast strains having reduced or increased glycerol production as the result of gene mutations are provided.

The present invention also provides a method for producing low glycerol producing mutant yeast strains. The method for selecting yeast mutants useful for low glycerol production includes the steps of initially treating a yeast strain with a mutagen, and then (a) selecting strains that show normal growth on rich media, (b) selecting strains that show osmo-sensitive growth on two different high osmolarity media, (c) eliminating strains which fail to grow on ethanol, (d) selecting strains that have reduced glycerol biosynthesis that can be traced to a defect in a single gene, (e) selecting strains that grow in 100 µg/ml hygromycin B, and in a preferred embodiment, (f) selecting strains that show decreased glycerol biosynthesis. In another preferred embodiment, the additional step (g) selecting strains that have decreased cytosolic levels of glycerol-3-phosphate dehydrogenase, and in a further preferred embodiment, (h) selecting strains with mutational defects that are complemented by genomic DNA with a defined origin in a chromosome selected from the group consisting of chromosome IV, chromosome XII, and chromosome X.

The invention also includes a method of using mutant yeast strains in fermentation and baking processes. A preferred method converts carbohydrates to ethanol or carbon dioxide via fermentation, with a lower than normal glycerol content in the fermentation products. The method comprises fermenting a nutrient medium containing a suitable carbohydrate substance with a mutant yeast strain of the genus Saccharomyces, or of a related genus Torulaspora, which has a reduced ability to produce glycerol. Fermentation products may be obtained which contain less than about 70% of the amount of glycerol found in products produced by the unmutated parent strain. Preferred products have a glycerol content about 60% or more preferably about 50% relative to the products of the parental strain. Mutant yeasts produced according to the invention may be used to produce novel beverages, including beer, wine, ale, or sake or novel baked goods such as bread. These and other conventional techniques when used to accomplish the objectives of the inventions are well known in the art and are exemplified by the specific references cited below, which are incorporated by reference as if fully set out herein.

The mutant yeast strains are also useful in a method to isolate DNA segments which complement the mutated genes. The isolated complementing DNA may be inserted into a suitable vector adjacent to a known yeast promoter such as those disclosed in Kingsman et al., 185:329 (1990), or Rosenberg et al., *Methods in Enzymology* 185:341 (1990). The vector may be inserted into a microorganism of the genus Saccharomyces or Torulaspora to produce a transformed strain having greater glycerol production than the parental strain.

Two HOG genes have been cloned and sequenced, HOG1 and HOG2. A stretch of DNA sequence on chromosome IV of the yeast *Saccharomyces cerevisiae* was disclosed (Ronne, unpublished) as a data entry (Accession Code X58858) in the Genbank database. One end of this DNA sequence is identical to that of a portion of HOG2 (see below). However, the functional significance of the Genbank X58858 data entry that overlaps with the HOG2 sequence was not previously investigated.

We started with a hog2-1 mutant that produced less glycerol than wild-type. We cloned a genomic fragment that complemented this defect and sequenced the DNA revealing the entire HOG2 gene. The present invention discloses the functional significance of the entire sequence complementing the hog2-1 mutant and the data demonstrate that deletion-disruption of a portion of the protein coding region of this sequence results in the reduction in glycerol production and increase in ethanol production.

High glycerol producing strains can be obtained by increasing the number of copies of the gene in the yeast cells. In one embodiment a HOG gene is inserted into a plasmid vector (YEp vector) that is maintained as many copies per cell. Techniques for inserting DNA segments into the plasmid vector are described by Rose and Broch, *Methods in Enzymology* 185:234 (1990). Alternatively, a HOG gene may be inserted into a plasmid vector (YIp vector) that can be inserted in yeast chromosomal DNA in multiple copies as described by Moir and Davidow, *Methods in Enzymology* 194:491 (1991). An additional alternative is to remove the promoter from the gene and replace it with a stronger promotor, all on a vector. In a preferred method, the promoterless gene is inserted in front of a strong promotor on either a multicopy vector or a vector that will be integrated into the yeast genomic chromosomes in multiple copies. A transformed yeast cell is a cell that has been treated with a vector, plasmid, or other technique to introduce additional DNA into the cell in a manner so that the additional DNA is expressed.

It is desirable to have such DNA segments to produce shuttle vectors which can be used to enhance glycerol production by causing over expression of the HOG genes in transformed yeast strains or to reduce glycerol production by targeted disruption of the chromosomal HOG gene using an in vitro mutated DNA segment as described by Rothstein, *Methods in Enzymology* 194:281 (1991).

It is an object of this invention to produce low glycerol fermentation products using mutant yeast strains. It is an object of this invention to provide novel mutant yeast strains that have a reduced glycerol production relative to the unmutated parental strain. It is a further object of this invention to provide a method for selecting yeasts with lower than normal glycerol production. It is also an object of this invention to use the low glycerol producing mutants to identify genes regulating glycerol production in yeasts. An additional object of this invention is to provide DNA segments which include a gene affecting glycerol synthesis. It is an object of this invention to provide a vector for the introduction of genes affecting glycerol production into transformed yeast cells to cause altered production of glycerol when desired. It is a further object of this invention to provide mutant, low glycerol-producing yeast strains by the device of gene deletion-disruption. Specifically, the three genes called HOG1, HOG2, and HOG4 have been deleted and disrupted singly and in pairwise combination in yeast stains to produce mutant strains with a reduction in glycerol biosynthesis.

This invention also provides mutant, low glycerol-producing yeast strains by the device of gene deletion-disruption. Specifically, the two genes called HOG1 and HOG2 have been deleted and disrupted singly and together in yeast strains to produce mutant strains with a reduction in glycerol biosynthesis.

HOG1 and HOG2 are defined as those yeast genomic DNA segments capable of complementing the reduced growth in high osmolarity media (defined as the $Osm^S$ phenotype) and glycerol biosynthesis defect of the hog1 and hog2 mutants (also called hog1-1 and hog24), respectively, as described below. In another embodiment the invention provides the DNA sequences of the HOG 1 and HOG2 genes. The invention in other embodiments combines the HOG 1 and HOG2 genes with vectors to provide novel transformed cells. In another embodiment deletion-disruption mutants are provided. These and other advantages of the present invention will become apparent from the following detailed description.

DESCRIPTION OF THE DRAWINGS

FIG. 5. Nucleotide sequence of HOG1 DNA and predicted amino acid sequence of the protein obtained on expression of the HOG1 gene. The Bal 1 and Sal I sites marked with ▼ border the fragment deleted in the construction of hog1-Δ.

[1-$^{13}$C]-glucose; (◊) [2-$^{13}$C]-ethanol; (■) 4×[1-$^{13}$C]-glycerol.

Figure 8A:
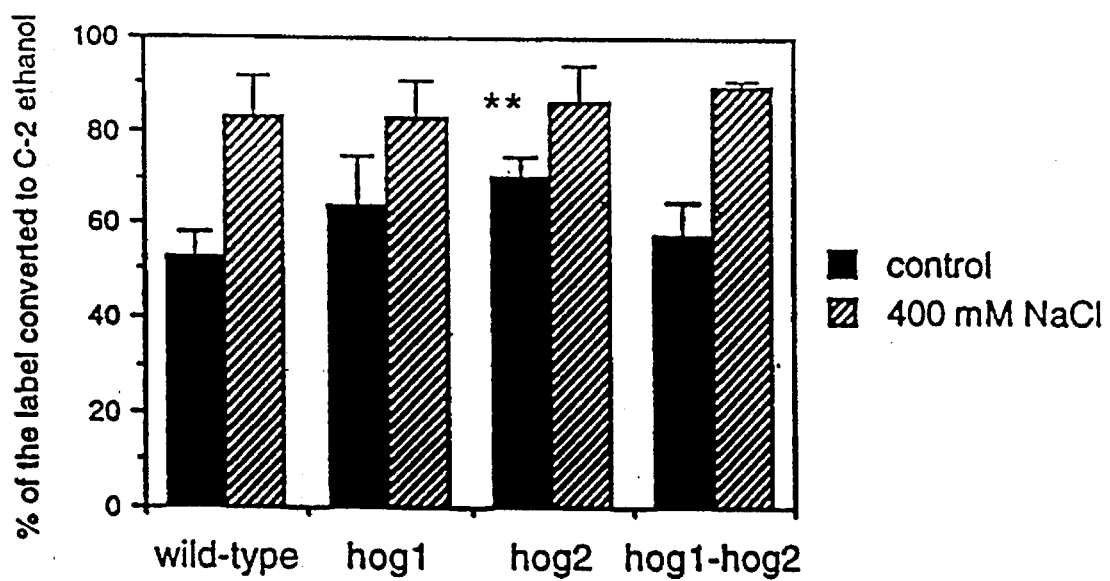

FIG. 8. Final yields of major fermentation endproducts for wild-type (YPH499), hog1 (JBY10), hog2 (JBY20), hog1-hog2 (JBY12) in control media and in media containing an additional 400 mM NaCl. For (A) [2-$^{13}$C]-ethanol and (B) [1-$^{13}$C]-glycerol, the yields are expressed as a percentage of the initial [1-$^{13}$C]-glucose. Means marked with ** over them are significantly different (p<0.05, Student's t-test) from those of the wild-type strain assayed under the same conditions.

Figure 9:
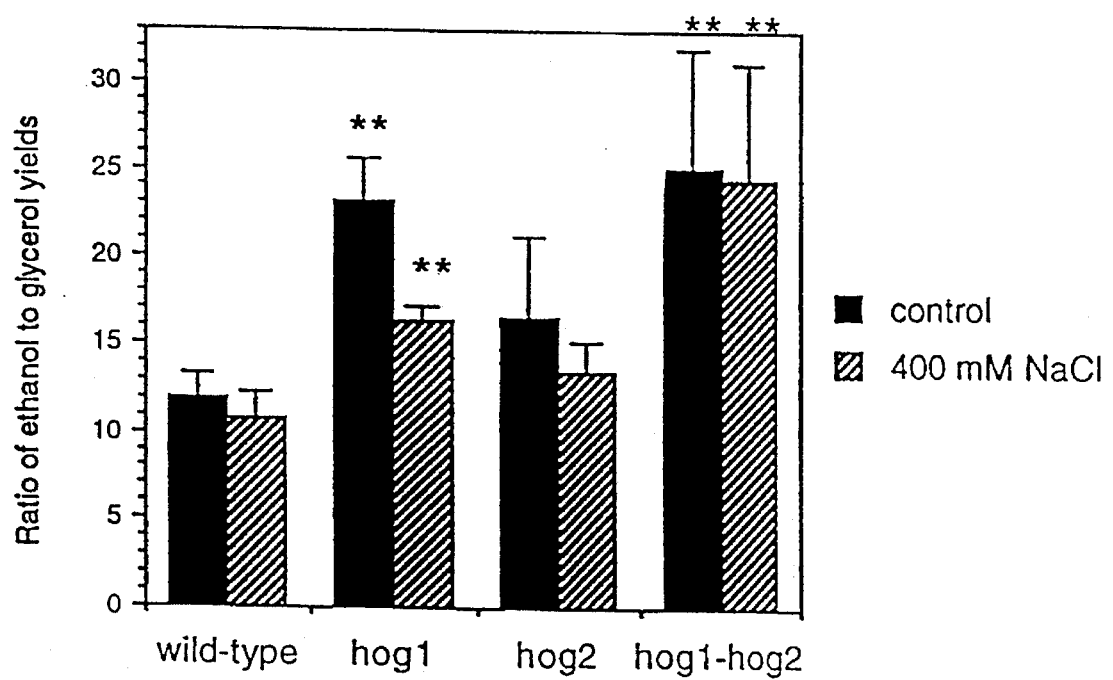

FIG. 9. Ratio of [2-$^{13}$C]-ethanol to [1-$^{13}$C]-glycerol yield in fermentations of [1-$^{13}$C] -glucose. by wild-type (YPH499), hog1 (JBY10), hog2 (JBY20), hog1–hog2 (JBY12) in control media and in media containing an additional 400 mM NaCl. Means marked with ** over them are significantly different (p<0.05, Student's t-test) from those of the wild-type strain assayed under the same conditions.

Figure 10:
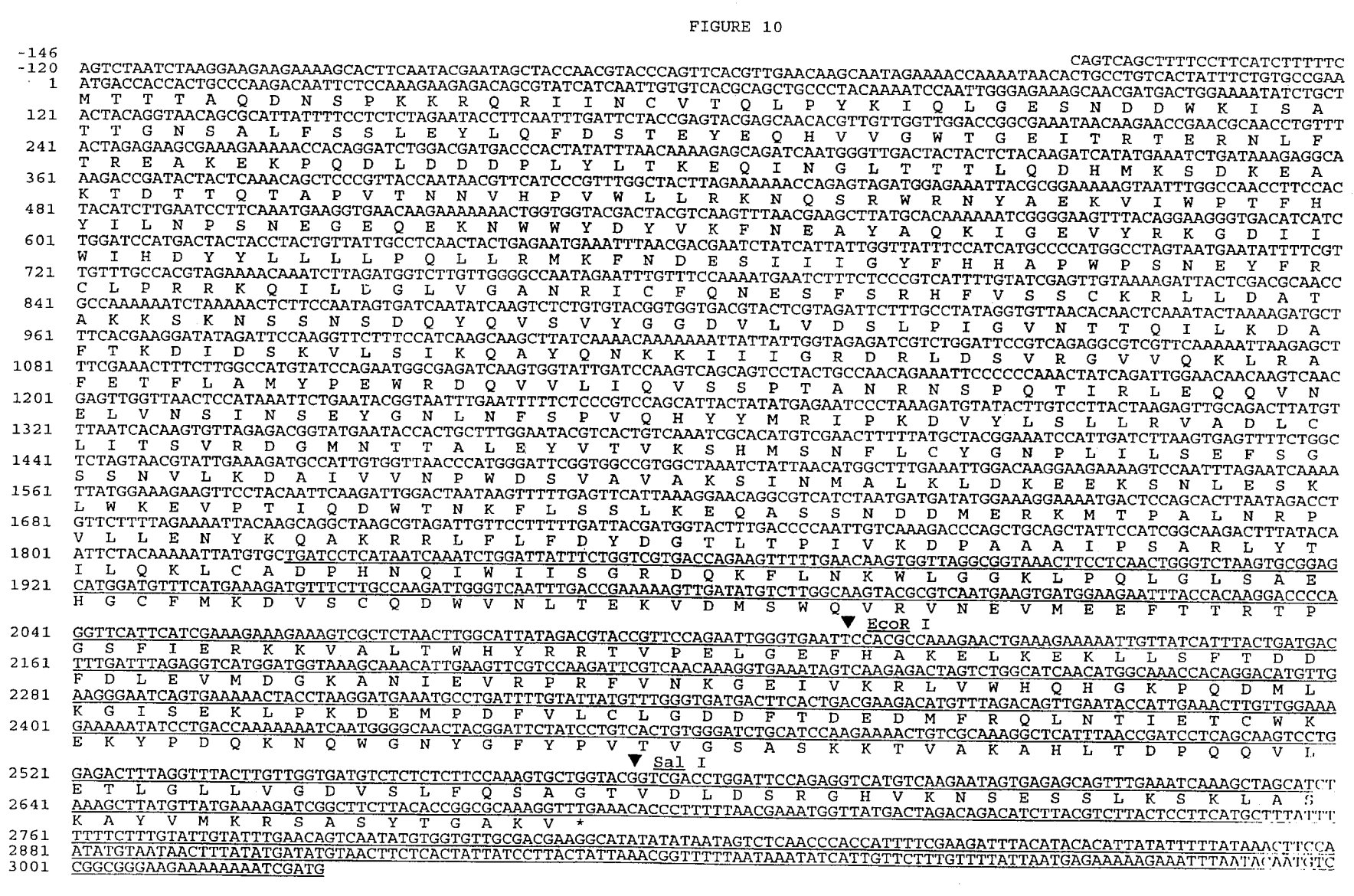

FIG. 10. Nucleotide sequence of HOG2 DNA and predicted amino acid sequence of the protein expressed by the HOG2 gene. The EcoR I and Sal I sites marked with (▼) border the fragment deleted in the construction of hog2-Δ1. Underlined nucleotide sequence is the previously disclosed sequence outside of the PPH3 protein coding region at its 5' end (Genbank accession code X58858).

DETAILED DESCRIPTION OF THE INVENTION

The present invention provides a mutant yeast strain which can be used under normal fermentation conditions in a commercial fermentation process to convert a carbohydrate substrate to ethanol or carbon dioxide with a reduced amount of glycerol in the fermentation product. Suitable microorganisms are yeasts of the well known genus Saccharomyces or of the well known genus Torulaspora. Preferably, the yeast will be a mutant strain of a commercial brewer's, vintner's, or baker's yeast. Such commercial yeasts include *Saccharomyces cerevisiae* var. *elliopsoideus*, *Saccharomyces leeticus*, *Saccharomyces bayonus*, *Saccharomyces carlsbergensis*, *Saccharomyces uranum*, *Saccharomyces vini*, *Saccharomyces oviformis*, *Saccharomyces chevalieri*, *Saccharomyces fermentati,* and *Saccharomyces rosei*. According to a recent systematic yeast nomenclature, all of the preceding yeast species, except for the last two, are more properly classified as species *Saccharomyces cerevisiae* Hansen, while the last two are more properly classified as *Torulaspora delibrueckii* Lindner (Barnett, Payne, and Yarrow, A Guide to Identifying and Classifying Yeasts, Cambridge University Press (1979)).

The carbohydrates which can be utilized by the yeast strains of the present invention include any of the starch or sugar containing materials normally fermented to form ethanol or carbon dioxide, including, for example, grapes, any of the various grains, potatoes, or certain other tuberous vegetables, any of the various berries, and of these various fruits, and the like. The fermentations are normally run under the usual fermentation conditions employed with a non-mutant strain of the same yeast. The mutant strain is selected by the methods of the invention and the medium containing a suitable substrate is inoculated. When starch is used as a substrate, it must first be chemically, biologically, or enzymatically partially converted ("malted") to sugar. The fermentation product may then be further treated to produce a beverage such as beer, wine, ale, or sake by conventional techniques.

It is preferred that glycerol production be reduced to at or about 70% of the glycerol production of the conventional parent strain. It is particularly preferred that the glycerol content in the fermentation product be no more than about 60%, and most preferably, reduced to less than 50%, of that produced by the non-mutant parent strain of the same yeast. Biologically pure cultures may be isolated by the selection method of the invention. The cultures are characterized by decreased glycerol production relative to the parent strain. A biologically pure culture is suitable for use in fermentation processes to achieve a desired fermentation product free of pathogens.

In accordance with the present invention, solids from the fermentation process may be normally separated from the other fermentation products, dried and further processed as animal feed or for other purposes. Because of their reduced glycerol content, the recovered solids require less time, expense, and energy to dry, thus making the overall fermentation process quicker, less costly, and more efficient. Fermentation solids may also be dried and further processed to produce useful products such as animal feeds or soil supplements.

In another embodiment, a mutant strain, produced according to the invention, may be used as a leavening agent in baked goods to give a product with lowered glycerol content to achieve a variation of flavor or texture. When used as a leavening agent, the mutant yeast will be substituted for a commercial non-mutant yeast of the same strain and used as a substitute in conventional fashion whenever a low glycerol content is desired in the finished baked goods. Glycerol content of baked goods influences taste, aroma, and texture, with desirable changes being noted when low glycerol strains are utilized. The mutant yeasts may be used to produce novel breads, rolls, and the like.

Although any yeast strain may produce a proper mutant strain having the desired characteristics, it is preferred to use haploid strains of commercial yeasts with good sporulation, good spore viability, and good growth of spore clones. Although mutants with the desired characteristics are expected to be more easily selected from haploid strains, useful mutants may also be obtained from diploid or polyploid parental stacks. A particular strain that has produced useful mutants, according to this invention, is a haploid strain derived from *Saccharomyces cerevisiae* S288C.

The mutagen used to produce a desired mutant species may be any mutagenic agent such as ultraviolet light, x-ray or gamma radiation, or any ionizing radiation, or a chemical mutagen such as nitroso-guanidine, ethyl methanesulfonate, or any other chemical which causes changes in genomic material or cellular DNA without killing all cells of a treated population.

Glycerol-3-phosphate dehydrogenase (GPDH; enzyme commission no. 1.1.1.94) activity is the rate limiting enzyme for glycerol biosynthesis in *Saccharomyces cerevisiae*. This cytosolic enzyme catalyzes the conversion of dihydroxyacetone phosphate to glycerol-3-phosphate, coupling this reaction to the oxidation of NADH. The specific activity (in $\mu$mole . min$^{-1}$ . mg protein$^{-1}$) of GPDH depends on the osmolality of the growth media in which the cells are grown prior to extraction and assay by the method described in Blomberg and Adler, *J. Bacteriol.* 171:1087 (1989). Other genes may also directly or indirectly influence glycerol production, and mutations of these genes may also be selected by the methods of the invention. In a preferred embodiment, a novel mutant yeast species having lower than normal glycerol production with enhanced ability to grow in glycerol media is produced by selective mutation in chromosome IV.

Figure 2:
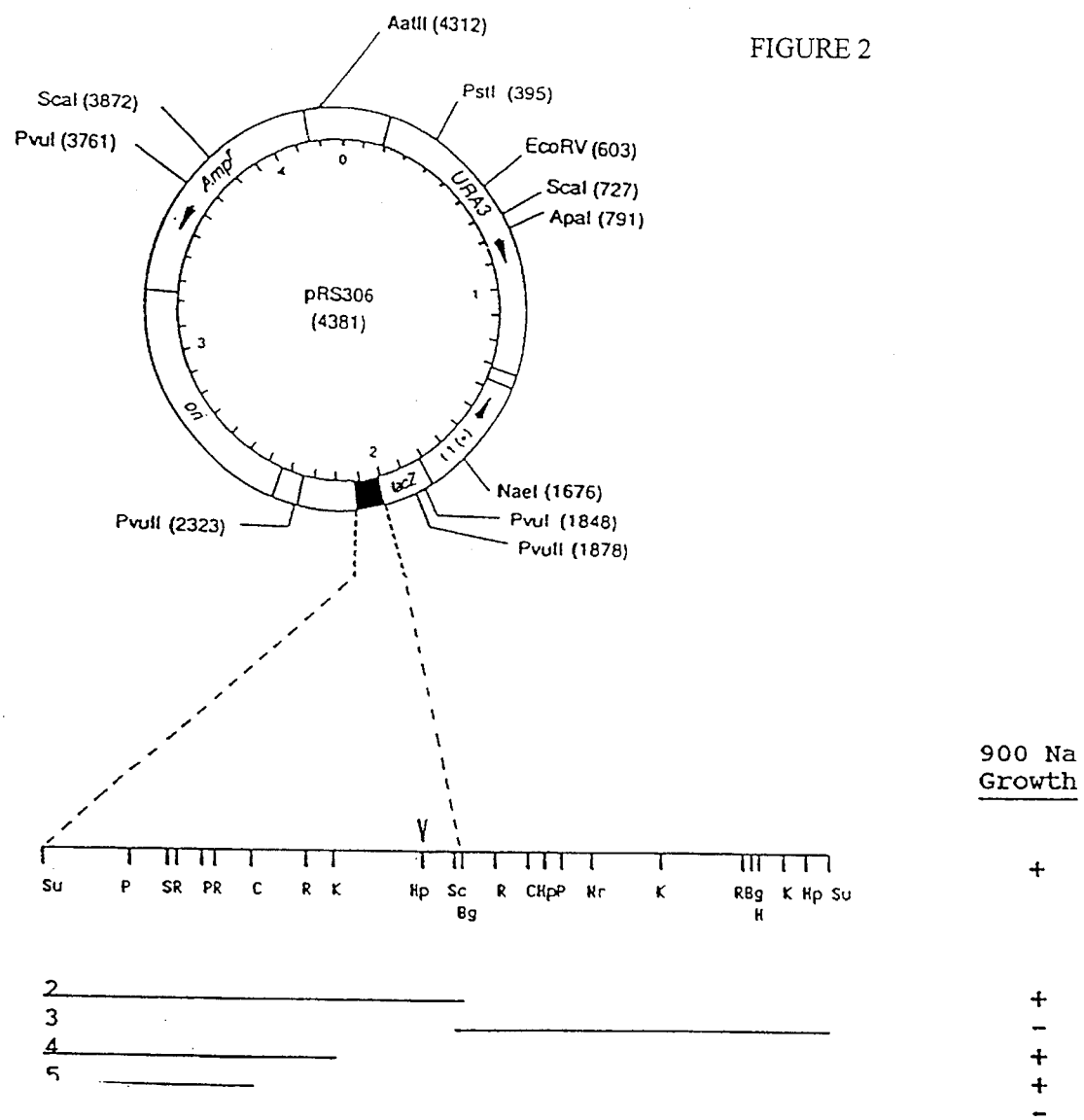
FIG. 2. A chart showing, in the middle of the figure, the restriction endonuclease cleavage sites in a fragment of genomic DNA isolated from a genomic DNA library and carried on the vector YCP50 which complements the hog1 phenotype of reduced growth on YEPD plus 900 mM NaCl. Shown at the bottom of the figure, below the original clone, are subcloned fragments carried on the vector pRS316 which either complement (+) or fail to complement (−) the 900 mM NaCl-YEPD growth phenotype of hog1. The fragment contained between the dashed lines was inserted into the multiple cloning site (black area) of the pRS306 vector whose restriction map is shown at the top of the figure.
Figure 3:
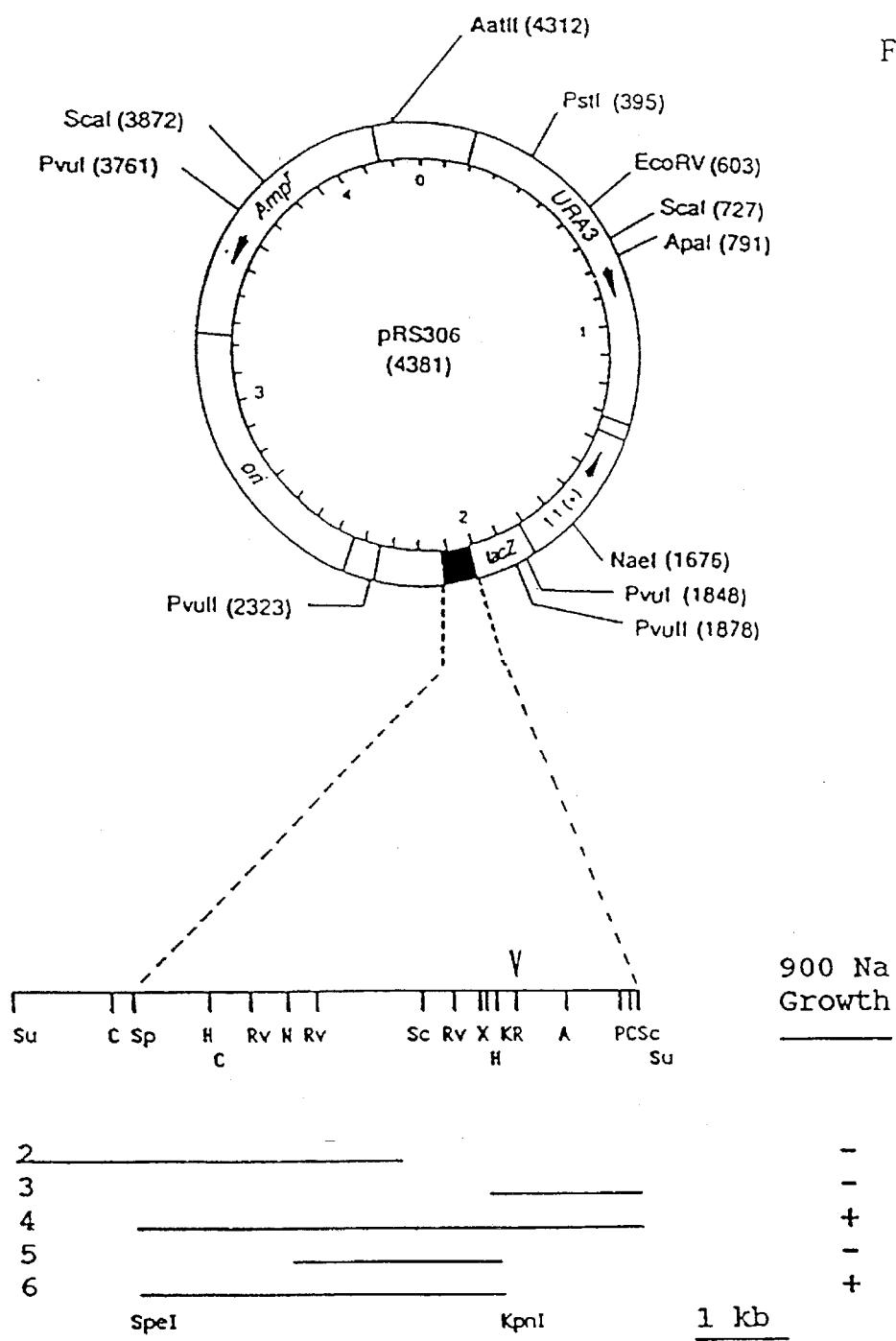
FIG. 3. A chart showing, in the middle of the figure, the restriction endonuclease cleavage sites in a fragment of genomic DNA isolated from a genomic DNA library and carried on the vector YCP50 which complements the hog4 phenotype of reduced growth on YEPD plus 900 mM NaCl. Shown at the bottom of the figure, below the original clone, are subcloned fragments carried on the vector pRS316 which either complement (+) or fail to complement (−) the 900 mM NaCl YEPD growth phenotype of hog4. The fragment contained between the dashed lines was inserted into the multiple cloning site (black area) of the pRS306 vector whose restriction map is shown at the top of the figure.

The novel yeast mutants have also been used in a novel method to isolate genomic DNA segments complementing the low glycerol producing mutant genes. Restriction endonuclease cleavage site maps of the genomic DNA clones are shown in FIGS. 2 and 3.

The complementing genomic DNA clones were introduced by conventional techniques into yeast—*E. coli* shuttle vectors which preferably contain one or more suitable markers. The clones were further tested for the unmutated or wild-type HOG gene by making a sub-clone and integrating the yeast vector, the sub-clone, and the marker gene into the genome of a mutant low glycerol producing strain. Integration was directed to the mutant locus by cutting the sub-clone with Hpa I which only cleaves in the inserted genomic DNA. Directed integration of the sub-clone with its vector created tandem, tightly linked copies of the gene, one mutant, and the other wild-type (un-mutated), together with the marker gene of the vector. Crossing the transformed yeast with an un-mutated, but marker-bearing strain produced haploid progeny highly predominate $Osm^r$ bearing the un-mutated gene, demonstrating the tight linkage of mutant wild-type genes in the transformed yeast. Different segments of genomic DNA from the original clone may be subcloned into the pRS316 vector and the resulting plasmids transformed into the mutant. By this method the DNA complementing each mutated gene may be isolated, restriction-mapped and localized to specific restriction cleavage fragments. The complementing fragments may then be amplified in *E. coli* on a plasmid or by known methods such as those disclosed in U.S. Pat. Nos. 4,683,195 and 4,683,202 and inserted into vectors by conventional methods as disclosed in Examples 2 and 3 below, or combined with known promoter genes such as those disclosed in Kingsman et al., *Methods in Enzymology* 185:329 (1990) or Rosenberg et al., *Methods in Enzymology* 185:341 (1990). Further, promoter-gene fusions may be subcloned into vectors allowing multiple copies of the fusion to be transformed into and expressed in yeast. The vectors are disclosed in Rose and Broach, Methods in *Enzymology* 185:234 (1990), and Moir and Davidow, *Methods in Enzymology* 194:491 (1991), and used to cause enhanced production of glycerol in transformed yeast cells produced by insertion of promoter and un-mutated HOG genes into yeast strains to obtain fermentation products having increased glycerol relative to the untransformed parental strains. The techniques for such insertion, vector construction, cell transformation, and selection of transformed cells are well known in the art. For example the techniques are described in Sambrook, Fritsch, and Maniatis, *Molecular Cloning, A Laboratory Manual*, 2nd Edition, Cold Spring Harbor Laboratory Press, Cold Spring Harbor (1989). Novel transformed strains so produced may in turn be used to produce novel wines, other novel beverages, novel baked goods, or in fermentations to produce glycerol as a recoverable product. The mutant-complementing DNA fragment or fragments may be mutated in vitro and transformed into a yeast strain to cause mutation of the homologous chromosomal gene or genes by homologous recombination. Novel transformed strains so produced may in turn be used in fermentations to produce novel wines, other novel beverages, novel baked goods, or in any other fermentations where reduction of glycerol content is desirable.

The following examples are offered to illustrate some embodiments of the present invention, but should not be read as limiting the scope of the invention.

EXAMPLE 1

Yeast cells (haploid strain derived from *Saccharomyces cerevisiae* S288C) were treated with the chemical mutagen, ethyl methanesulfonate, to induce mutations by the method disclosed by Lindegren, Hwang, Oshima, and Lindegren, *Can. J. Genet. Cytol.* 7:491 (1965). Mutated cells ($10^5$) were screened by replica plating for the ability to grow in (a) YEPD (1% yeast extract, 2% bactopeptone, 2% dextrose), (b) YEPD supplemented with 900 mM NaCl, (c) YEPG (1% yeast extract, 2% bactopeptone, 3% glycerol), (d) YEPE (1% yeast extract, 2% bactopeptone, 2% ethanol), and (e) YEPD supplemented with 1.8M sorbitol. The unmutagenized parental strain grew on all media. Only those mutants with the following growth properties (compared to the parental strain) were retained for further analysis: normal growth on normal rich media "a" and on either media "c" or "d"; slower growth on high osmolality media "b" and "e" (osmotic-sensitive, sometimes referred to below as $Osm^s$).

All $Osm^s$ mutant strains were analyzed for glycerol production in YEPD and in YEPD plus 400 mM NaCl after 1 hr. The enzymatic method used to measure both intracellular and total (extracellular and intracellular) levels of glycerol after heat-killing of the cells is disclosed by Frings, and Pardue, *Anal. Chim. Acta* 34:225 (1966). Glycerol production by the mutants compared to the parental strains is summarized in Table I. Only mutant strains containing recessive, nuclear, single-gene pre-selected mutations are retained. Recessive mutants are indicated when mutant heterozygous diploids (isolated from mating mutant x parental) have the same osmotic-resistance (growth on media "b" and "e") as the homozygous wild-type diploids (isolated from mating parental x parental). Nuclear, single gene mutations were inferred when growth of haploid progeny on media "b" and "e" segregated 2 growth:2 no growth after sporulation of heterozygous diploids and microdissection of asci into four separate haploid spores. Thus, recessive nuclear, single gene mutants are selected.

When *Saccharomyces cerevisiae* S288C was treated in the preceding method, the total number of novel mutants remaining after application of the selection criteria was 19, each containing a mutation in one of three genes by complementation analysis. To test for complementation, mutants were mated with each other and resultant diploids tested for $Osm^s$. If diploids were $Osm^s$, the mutations in the two strains were judged to be allelic with each other. If diploids were $Osm^r$, the mutations were judged to be in separate genes. The genes (the number of alleles of each is given in parentheses) are named the HOG1 (3), HOG2 (4), and HOG4 (12) genes. Complementation tests also demonstrate hog1, hog2, and hog4 were not allelic with either osm 1 or osm 2.

The growth of hog1, hog2, and hog4 was insensitive to hygromycin B (100 µg/ml in YEPD). Genetic crosses show that the hog1, hog2, and hog4 mutations are unlinked, i.e., that HOG1, HOG2, and HOG4 are separate genes.

Genetic linkage analysis showed that, for the hog1, hog2, and hog4 mutations, the defect in synthesis of glycerol is due to the same mutation that causes osmotic-sensitive growth. Progeny of a genetic cross of hog1-1×wild-type showed 2:2 co-segregation of $Osm^s$ growth and decreased ability to accumulate intracellular glycerol. The hog1 and hog4 mutation also confers the ability to grow better than wild-type on YEPG medium.

Figure 1:
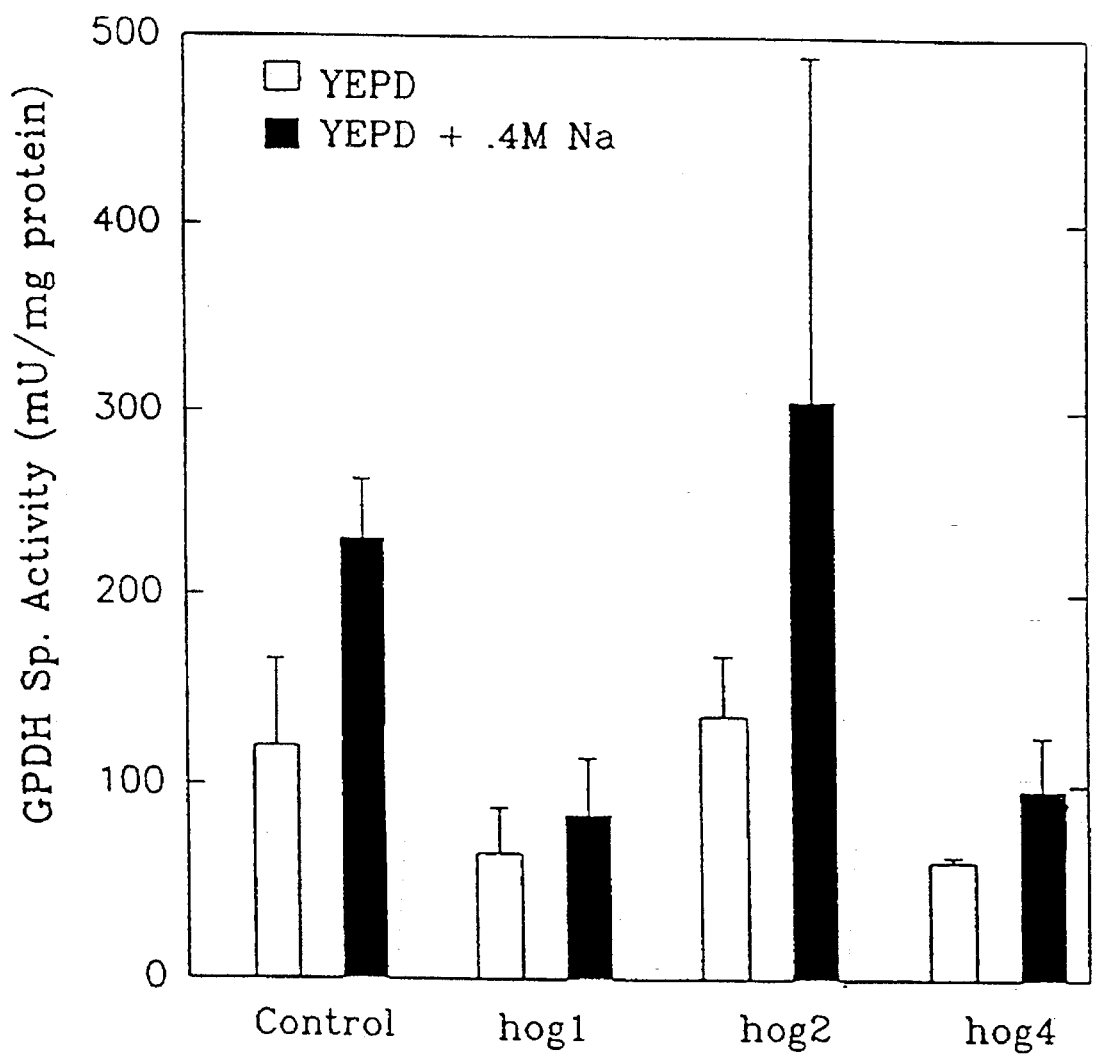
FIG. 1. A chart showing the specific activity of Glycerol-3-phosphate dehydrogenase (GPDH) in desalted cell extracts from four strains: a control strain, a hog1 mutant strain, a hog2 mutant strain, and a hog4 mutant strain grown either in YEPD Or in YEPD plus 0.4M NaCl. The hog1 and hog4 strains (but not the hog2 strain) have reduced GPDH specific activity relative to the control strain.

Growing on medium "a", the doubling times of hog1, hog2, and hog4 mutants, respectively, compared to wild-type were the following: wild-type 1.56 hr., hog1 1.38 hr., hog2 2.10 hr., hog4 1.56 hr. As shown in FIG. 1, hog1 and hog4 mutations, relative to the wild-type parent, cause a significant decrease in the specific activity of GPDH in desalted cell extracts. The hog2 mutation has no effect on the specific activity of GPDH.

Certain mutant yeast strains isolated by the procedure set out above were deposited at Agricultural Research Culture Collection U.S.D.A. A.R.S. 1815 N. University Peoria, Ill. on May 21, 1991 Strain ND2-4A genotype alpha ura3-52 hog1 is identified as NRRL Y18828; Strain ND12-4D genotype alpha ura3-52 hog2 is identified as NRRL Y18826; and Strain JB15-6A genotype alpha ura3-52 hog4 is identified as NRRL Y18827.

TABLE I

| Allele Strain designation) | Glycerol* (mean ± S.D.) | YEPD (252 mos.) % Reduction | Glycerol* (mean ± S.D.) | YEPD + .4M NaCl (1003 mos.) % Reduction |
|---|---|---|---|---|
| 9A(parental) | 40 ± 10 | | 188 ± 48 | |
| hog1 | | | | |
| 1 (ND2) | 23 ± 8 | 58 | 95 ± 42 | 51 |
| 2 (DAC16) | 38 ± 13 | 95 | 98 ± 5 | 52 |
| 3 (DAD3) | 30 ± 4 | 75 | 128 ± 13 | 68 |
| hog2 | | | | |
| 1 (ND12) | 30 ± 13 | 75 | 83 ± 5 | 44 |
| 2 (ND17) | 30 ± 25 | 75 | 108 ± 15 | 57 |
| 3 (ND33) | 25 ± 3 | 63 | 90 ± 18 | 48 |
| 4 (ND35) | 35 ± 14 | 88 | 78 ± 15 | 41 |
| hog4 | | | | |
| 1 (JB15) | 25 ± 3 | 63 | 88 ± 14 | 47 |
| 2 (ND1) | 20 ± 15 | 50 | 83 ± 6 | 44 |
| 3 (ND11) | 20 ± 5 | 50 | 60 ± 43 | 32 |
| 4 (ND26) | 13 ± 3 | 33 | 78 ± 15 | 41 |
| 5 (ND36) | 23 ± 5 | 58 | 90 ± 10 | 48 |
| 6 (DAA1) | 35 ± 20 | 88 | 133 ± 10 | 71 |
| 7 (DAA3) | 28 ± 3 | 70 | 100 ± 40 | 53 |
| 8 (DAA4) | 18 ± 3 | 45 | 93 ± 10 | 49 |
| 9 (DAA6) | 28 ± 3 | 70 | 153 ± 53 | 81 |
| 10 (DAD4) | 13 | 33 | 115 | 61 |
| 11 (DAE9) | 15 | 38 | 38 | 20 |
| 12 (DAE10) | 28 ± 3 | 70 | 78 ± 20 | 41 |

% reduction = $\frac{\text{mutant glycerol}}{\text{parental glycerol}} \times 100$

*measured in nmols/$10^7$ cells

The mutant yeasts of the present invention are useful for converting any carbohydrate which is normally fermentable into an ethanol containing fermentation product having a reduced glycerol content. The invention is especially useful when a tart or "dry" flavor is desired in a fermented beverage, or when solids are to be recovered from the fermentation products and subsequently dried, as in, for example, production of animal feeds from the solids recovered in beer production. The mutant yeasts of the invention are also useful as a leavening agent in baked goods where a crisp, dry texture or less sweet flavor is desired.

EXAMPLE 2

The hog1 mutant can be complemented by a segment of genomic DNA cloned from *Saccharomyces cerevisiae*. A 9.6 kilobase (kb) segment of genomic DNA was isolated from the genomic library described by Rose, et al., Gene 60:237 (1987). This clone complemented both phenotypes of the hog1 mutation: $Osm^s$ and reduced glycerol synthesis. The restriction endonuclease cleavage site map of this genomic DNA clone is shown in FIG. 2. Restriction sites shown are the following: Su, Sau 3A/BamH I; P, Pst I; S, Sal I; R, EcoR I, C, Cla I; K, Kpn I; Hp, Hpa I; Sc, Sac I; Bg, Bgl II; Nr, Nru I; H, Hind III.

Various subclones were constructed in the YCp50 (Rose, et al.,supra ), or pRS316 vector (Sikorski, and Hieter, Genetics 122:19 (1989)), and introduced into a hog1 ura3 strain by selecting $Ura^+$. Transformed yeasts containing different subclones were checked for growth in YEPD plus 900 mM NaCl. The smallest subclone (#8) that still complemented hog1 when carried on the pRS316A vector was approximately 2.1 kilobases (kb).

To test whether the genomic clone contains the wild-type HOG1 gene, a subclone (#2) was inserted into the multiple cloning site of the integrating yeast vector pRS306 which was used to integrate, by homology, the subclone and the URA3 marker of the vector into the genome of a hog1 ura3 strain. Integration was directed to the hog1 locus by cutting the resulting plasmid with Hpa I which only cleaves in the inserted genomic DNA. If the genomic clone contains the HOG1 gene, directed integration of the subclone with its vector is predicted to create tandem, tightly-linked copies of the gene, one mutant (hog1), the other wild-type (HOG1), together with the URA3 gene of the vector. An $Osm^r$ $Ura^+$ transformed yeast was crossed to a HOG1 URA3 strain and the resulting diploid sporulated. Only one of the haploid progeny in 23 tetrads from this genetic cross was $Osm^s$. Tight linkage of the hog1 and HOG1 genes, as predicted, was thus observed. Analysis of a second genetic cross between the transformed strain and a hog1 ura3 strain showed only the parental ditype (2:2 $Ura^+Osm^r:Ura^-Osm^s$) in 8 tetrads consistent with tight linkage between HOG1 and URA3 genes as expected for a directed integration of the entire plasmid. Thus, based on genetic and physical mapping evidence, the complementing genomic DNA contains the HOG1 gene, which is further localized to a 2.1 kb fragment bounded by Sau 3A/BamH I and EcoR I sites on either end. By this method DNA segments containing the HOG1 gene are available for insertion into yeast cells by conventional methods to produce transformed yeast strains with high glycerol production due to overexpression or expression of multiple copies of the HOG1 gene consistent with the predicted disruption of one copy of HOG1 in the diploid with the TRP1 -marked hog1-Δ1 mutation.

EXAMPLE 3

The hog4 mutant can be complemented by a segment of genomic DNA cloned from *Saccharomyces cerevisiae*. A 6.5 kilobase (kb) segment of genomic DNA was isolated from the genomic library described by Rose, et al., Gene 60:237 (1987). This clone complemented both phenotypes of the hog1 mutation: $Osm^s$ and reduced glycerol synthesis. In FIG. 3, the restriction endonuclease cleavage site map of this genomic DNA clone is shown at top (#1). Restriction sites shown are the following: Su, Sau 3A/BamH I; C, Cla I; Sp, Spe I; H, Hind III; Rv, EcoR V; N, Nhe I; Sc, Sac I; X, Xba I; K, Kpn I; R, EcoR I; A, Apa I; P, Pst I.

Various subclones were constructed in the YCp50 (Rose, et al., (1987), or pRS316 vector (Sikorski, and Hieter, Genetics 122:19 (1989)), and introduced into a hog4 ura3 strain by selecting $Ura^+$. Transformed yeasts containing different subclones were checked for growth in YEPD plus 900 mM NaCl. The smallest subclone (#6) that still complemented hog4 when carried on the pRS316 vector was approximately 3.8 kb.

To test whether the genomic clone contains the wild-type HOG4 gene, a subclone (#4) was inserted into the multiple cloning site of the integrating yeast vector pRS306 which was used to integrate, by homology, the subclone and the URA3 marker of the vector into the genome of a hog4 ura3 strain. Integration was directed to the hog4 locus by cutting the resulting plasmid with EcoR I which only cleaves in the inserted genomic DNA. If the genomic clone contains the HOG4 gene, directed integration of the subclone with its vector is predicted to create tandem, tightly-linked copies of the gene, one mutant (hog4), the other wild-type (HOG4), together with the URA3 gene of the vector. An $Osm^r$ $Ura^+$ transformed yeast was crossed to a HOG4 URA3 strain and the resulting diploid was sporulated. None of the haploid progeny in 19 tetrads from this genetic cross were $Osm^s$. Tight linkage of the hog4 and HOG4 genes, as predicted, was thus observed. Analysis of a second genetic cross between the transformed strain and a hog4 ura3 strain showed only the parental ditype (2:2 $Ura^+Osm^r$:$Ura^-Osm^s$) in 24 tetrads consistent with tight linkage between HOG4 and URA3 genes as expected for a directed integration of the entire plasmid. Thus, based on genetic and physical mapping evidence, the complementing genomic DNA contains the HOG4 gene, which is further localized to a 3.8 kb fragment bounded by Spe I and Kpn I sites on either end.

By this method DNA restriction enzyme cleavage fragments which contain the HOG1 gene are available for insertion into yeast cells by conventional methods to produce transformed yeast strains with high glycerol production by overexpression or expression of multiple copies of the hog4 gene. In a similar manner the HOG2 gene may be cloned, inserted, and expressed.

EXAMPLE 4

In a preferred embodiment the smallest HOG gene containing restriction enzyme DNA fragments from Examples 2 and 3 are inserted into yeast cells in multiple copies by the techniques described above. The resulting transformed yeasts are then substituted for untransformed strains in fermentation processes to produce glycerol in quantities in excess of 10 g/l.

The transformed yeasts of Examples 2, 3, or 4 may be used in conventional fermentation processes to produce novel high glycerol containing beverages including beer, wine, ale, and sake or baked goods including bread. High glycerol producing transformed yeasts of Examples 2 and 3 may also be used to produce glycerol in quantities in excess of 10 g/l.

EXAMPLE 5

In a preferred embodiment, HOG gene-containing fragment or fragments from Examples 2 and 3 are mutated in vitro. The mutated DNA fragment or fragments are then transformed into a yeast strain so as to cause mutation of the homologous chromosomal HOG gene or genes by the techniques described above. The resulting transformed yeasts are then substituted for untransformed strains in fermentation processes to produce glycerol in lower quantities. The transformed yeasts may produce about 70% of the glycerol produced by the unmutated parent, preferably 60% and more preferably producing less than 50% relative to the unmutated parent.

The transformed yeasts of Example 5 may be used in conventional fermentation processes to produce novel low glycerol containing beverages including beer, wine, ale and sake, or baked goods including bread or other fermentation products.

EXAMPLE 6

HOG1 was cloned from a yeast genomic library on the centromere vector YCp50 (Rose, M., Winston, and Hieter, *Methods in Yeast Genetics,* Cold Spring Harbor Laboratory Press, Cold Spring Harbor (1990)), by complementation of the $Osm^s$ phenotype of the hog1-1 mutant. The genomic fragment that complemented the $Osm^s$ and reduced glycerol biosynthesis phenotypes of hog1-1 was 9.7 kilobases (kb). To test whether HOG1 had been cloned, the chromosomal locus corresponding to the cloned DNA was marked with a selectable marker and shown to be tightly linked to the corresponding mutation. The restriction map of the original hog1-1 complementing clone is shown in FIG. 2. To further delineate the HOG1 gene, fragments of the genomic insert were subcloned into centromere vectors and tested for complementation of the $Osm^s$ phenotype of the hog1-1 mutant. Using this approach, HOG1 was localized to a 2.5 kb Cla I-BamH I fragment. Media for these experiments was prepared as described in Rose, et al. (1990). Yeast were grown at 30° C. Transformation of yeast was performed using the LiCl procedure (Ito, Fukuda, Murata, and Kimura, *J. Bacteriol:* 153:163 1983)). Transformants were selected on synthetic complete (SC) media lacking uracil or tryptophan. Yeast genomic DNA for Southern hybridizations was isolated as described in Rose, et al. (1990). *E. coli* strains HB101 or SURE™ (Stratagene) were used for transformations. Plasmid DNA was isolated from *E. coli* by alkaline lysis (Sambrook, Fritsch, and Maniatis, *Molecular Cloning, A Laboratory Manual,* 2nd Edition, Cold Spring Harbor Laboratory Press, Cold Spring Harbor (1989)) and from yeast (Hoffman, and Winston, *Gene* 57:267 1987)). Southern blot hybridization of HOG1 to electrophoretically-separated Saccharomyces cerevisiae chromosomes showed hybridization of HOG1 to chromosome XII. The Cla I-BamH I genomic DNA fragment containing HOG1 (see FIG. 4) was sequenced. A plasmid containing HOG1 on a 2.5 kb Cla I-BamH I genomic DNA fragment was purified by banding in a CsCl density gradient and the sequence of the genomic DNA fragment determined on both strands. (Sanger, Nicklen, and Coulsen, *Proc. Nat. Acad. Sci.* USA 74:5463 (1977)). The nucleotide sequence shown in FIG. 5 revealed a large open reading frame (ORF), 1.2 kb long, with a predicted protein of 416 amino acids with a molecular weight of 47 kDa. Complementation of hog-1 required an intact EcoR I site 0.5 kb from the Cla I site. This EcoR I site is located several nucleotides to the 3' side of the first ATG of this ORF. Northern hybridization using the cloned HOG1 gene as probe hybridized to a ~1.4 kb transcript, showing that HOG1 is expressed in vivo.

Figure 4A:
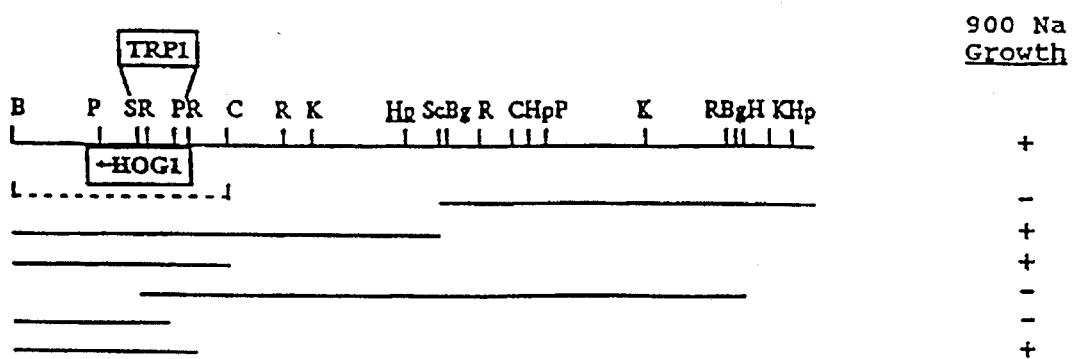
FIG. 4. Cloning of HOG1 and HOG2 and construction of deletion mutations in the HOG genes. Different fragments of genomic DNA were found to complement the $Osm^S$ phenotype of each hog complementation group. (+) indicates full complementation of the $Osm^S$ phenotype of the hog mutant; (±) partial complementation; (−) no complementation. Smaller restriction fragments of each original clone were introduced into a single copy vector (Sikorski, and Hieter, Genetics 122:19 (1989), transformed into a hog mutant, and the transformants tested for growth on plates containing YEPD+0.9M NaCl. Deletion-disruptions of each gene were constructed by replacing internal fragments of the complementing DNA with the marker shown. The 0.4 kb Bal I-Sal I fragment (sites marked ▼ in FIG. 5), containing part of the protein coding region of HOG1, was replaced with the TRP1 marker to create hog1-Δ1::TRP1, also called hog1-Δ1. HOG2 was disrupted by the replacement of the 0.5 kb EcoR I-Sal I fragment with URA3, creating hog2-Δ::URA 3, also called hog2-Δ1. HOG4 was disrupted by the replacement of the 2.9 kb Hind III-Hind III fragment with URA3, creating hog4-Δ1. The construction was digested with restriction enzymes which cut in the genomic DNA on each side of the marker and used to transform the wild type diploid YPH501 (MATa/MATatrp1/trp1 ura3/ura3, Sikorski, and Hieter, Genetics 122:19 (1989). Trp⁺ or Ura⁺ transformants were sporulated and subsequent tetrads analyzed. In each case, tetrads showed a 2:2 cosegregation of the Trp⁺ or Ura⁺ phenotype with $Osm^S$. Abbreviations of restriction enzymes include: B, BamH I; Bg, Bgl II; C, Cla I; H, Hind III; Hp, Hpa I; K, Kpn I; N, Nhe I; P, Pst I; R, EcoR I; S, Sal I; Sc, Sac I; Sp, Spe I; and X, Xba I. Dashed line under the HOG1 clone is the stretch of DNA whose sequence is shown in FIG. 5.
Figure 4B:
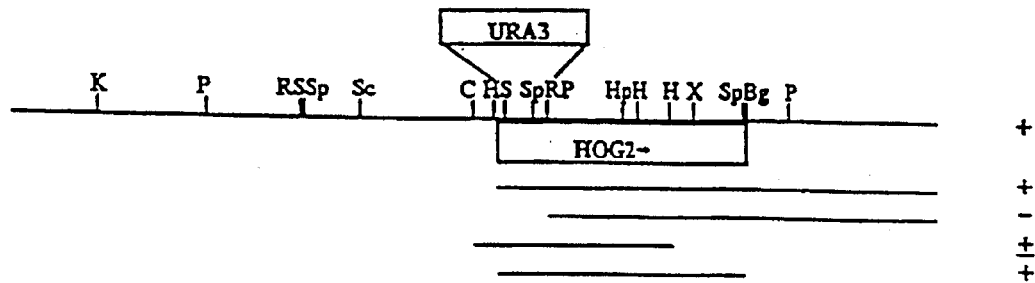
Figure 4C:
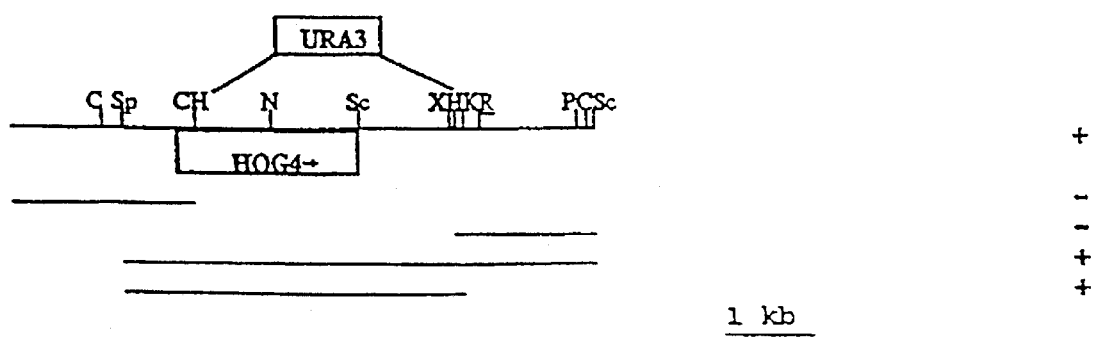

A deletion-disruption mutant of HOG1 was constructed by one-step genomic sequence replacement (Rothstein, *Meth. Enzym.* 101:228 (1991)), in which a 0.4 kb restriction fragment of HOG1 was deleted in vitro and replaced with the selectable marker TRP1. The plasmid pDA1 contains the 9.6 kb hog1-1-complementing genomic DNA fragment (FIG. 4). A 5.5 kb Hind III-Bg II fragment of complementating genomic DNA (including 150 bp from YCp50) was subcloned from pDA1 into the BamH I-Hind III sites of the pRS306 plasmid (Sikorski, and Hieter, *Genetics* 122:19 (1989)), to form the plasmid pJB1. The ~400 bp Bal I-Sal I fragment of pJB1 containing the first half of the coding sequence of HOG1 was replaced with a ~900 bp Sal I-Sma I fragment from pJJ280 (Jones, and Prakash, *Yeast* 6:363 1990)), containing the TRP1 marker. The TRP1-marked deletion mutation of HOG1 was excised from the plasmid by a Sca I-Cla I cut and used to disrupt one copy of HOG1 in YPH501. The transformed $Trp^+$ diploids were sporulated, tetrads microdissected, and the growth properties of the haploid progeny tested on synthetic complete media lacking tryptophan or on rich media (YEPD) containing 0.9M NaCl to test for an Osm$^s$ phenotype. In each tetrad, a 2:2 segregation of Trp$^+$ with Osm$^s$ was observed, consistent with the predicted disruption of one copy of HOG1 in the diploid with the TRP1-marked hog1-Δ1 mutation. Southern blot analysis of the mutant strain and YPH501 using the HOG1 gene as probe confirmed the deletion-disruption of HOG1 in the mutant.

Compared to a congenic wild-type control strain (YPH499), the deletion-disruption mutant hog1-Δ1 contained less intracellular glycerol (FIG. 6) and produced less total glycerol (Table II). Intracellular glycerol was measured using the procedure of Blomberg and Adler *J. Bacteriol.* 171:1087 (1989). A log-phase yeast culture containing 2×10$^7$ cells in 2 ml was diluted with 8 ml of either YEPD or YEPD plus 500 mM NaCl (final concentration of NaCl=400 mM). YEPD media contained 1% yeast extract, 2% bactopeptone, 2% dextrose, and 20 ug/ml adenine sulfate. The 0.4M NaCl concentration used to elicit glycerol accumulation was chosen because this concentration induced the largest stimulation of glycerol accumulation in a 1 hr incubation (range tested: 0.1–1.0M NaCl). NaCl concentrations higher than 0.4M require a longer lag phase before glycerol begins to accumulate in cells. After 1 hr at 30° C., cells were centrifuged and then resuspended in an isotonic saline solution (0.135M NaCl at 242 mOsm was isosmotic with YEPD; 600 mM NaCl at 1003 mOsm was isosmotic with YEPD plus 0.4M NaCl, all osmolalities determined by osmometer). Cells were washed by centrifugation in the isotonic NaCl solution. The cell pellet was resuspended in 500 μl of boiling distilled H$_2$O, boiled in a capped tube for 15 min. and stored at −20° C. Immediately prior to assay, samples were thawed and centrifuged at 13,000 rpm for 2 min. Aliquots of the supernatant were assayed for glycerol. The quantitation of glycerol was performed using a two step colorimetric assay that was a modification of that described by Frings and Purdue (1966). The assay mixture in a 1 ml cuvette contained 0.83 U of glycerol dehydrogenase (Sigma G3512) and 680 μM AND$^+$ in a coupled reaction. The NADH formed by this first reaction is oxidized by diaphorase in a reaction coupled to the reduction of DCPIP. The oxidized by diaphorase in a reaction coupled to the reduction of DCPIP. The oxidized form of this dye is blue, the reduced form is colorless. The rate of dye reduction and thus the rate of glycerol oxidation was measured by determining the rate decrease in absorbance at 600 nm. The initial rate of dye reduction was a linear function of glycerol concentration in the range between 25–250 μM glycerol.

Figure 7A:
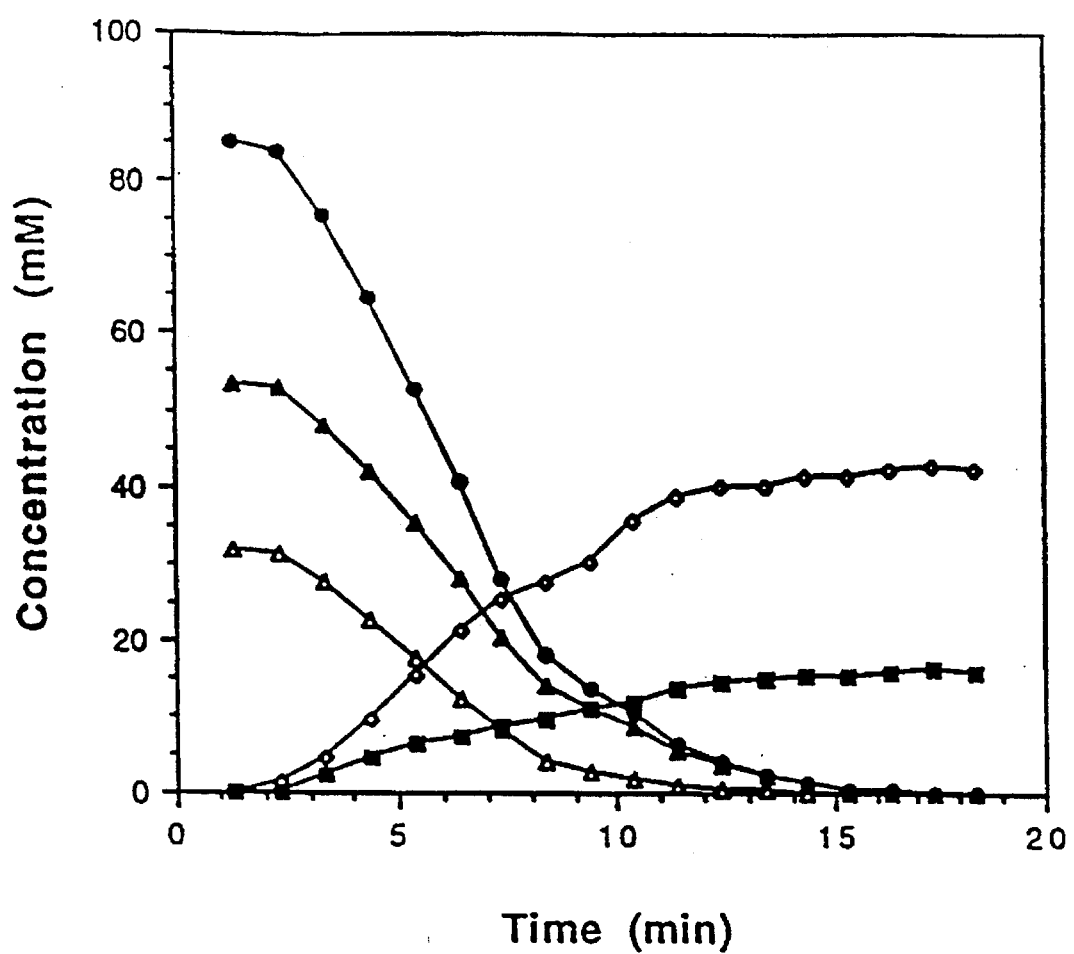
FIG. 7. Time course of yeast fermentation of [1-$^{13}$C]-glucose in control media (A) and in media containing 400 mM NaCl (B). The time course of changes in the concentrations of glucose, ethanol, and glycerol, measured by $^{13}$C nuclear magnetic resonance (NMR) spectroscopy are shown for YPH499, a control strain with the same genetic background as the mutant strains, but wild-type for HOG1 and HOG2. In the control condition, a yeast culture was grown to mid-logarithmic phase in YEPD (2% bactopeptone, 1% yeast extract, 2% dextrose). Cells were then washed out of this media into 0.85 g/l $KH_2PO_4$, 0.15 g/l $K_2HPO_4$, 0.5 g/l $MgSO_4$, 0.1 g/l NaCl in 50 mM $Na_2H_2P_2O_7$ buffer pH 6, and brought to a final concentration of 35.5% v/v in the same buffer. In the high osmolarity NaCl condition, all media and solutions were supplemented with 400 mM NaCl. [1-$^{13}$C]-glucose was added to a final concentration of 85 mM to start the fermentation at t=0. A 500 MHz NMR spectrometer (Bruker) was used to measure the concentrations of $^{13}$C-labeled metabolites during the fermentation. Spectra were taken at two minute intervals. Standards were used to identify the [1-$^{13}$C]-glycerol and [2-$^{13}$C]-ethanol peaks. The integrated signals originating from the glucose, ethanol and glycerol peaks were corrected for saturation and used to calculate the concentrations of these metabolites. Note that glycerol values have been multiplied by a factor of 4 to better visualize changes in this parameter. Symbols: (Δ) [1-$^{13}$C]1-α-glucose; (▲) [1-$^{13}$C]-β-glucose; (●) total
Figure 7B:
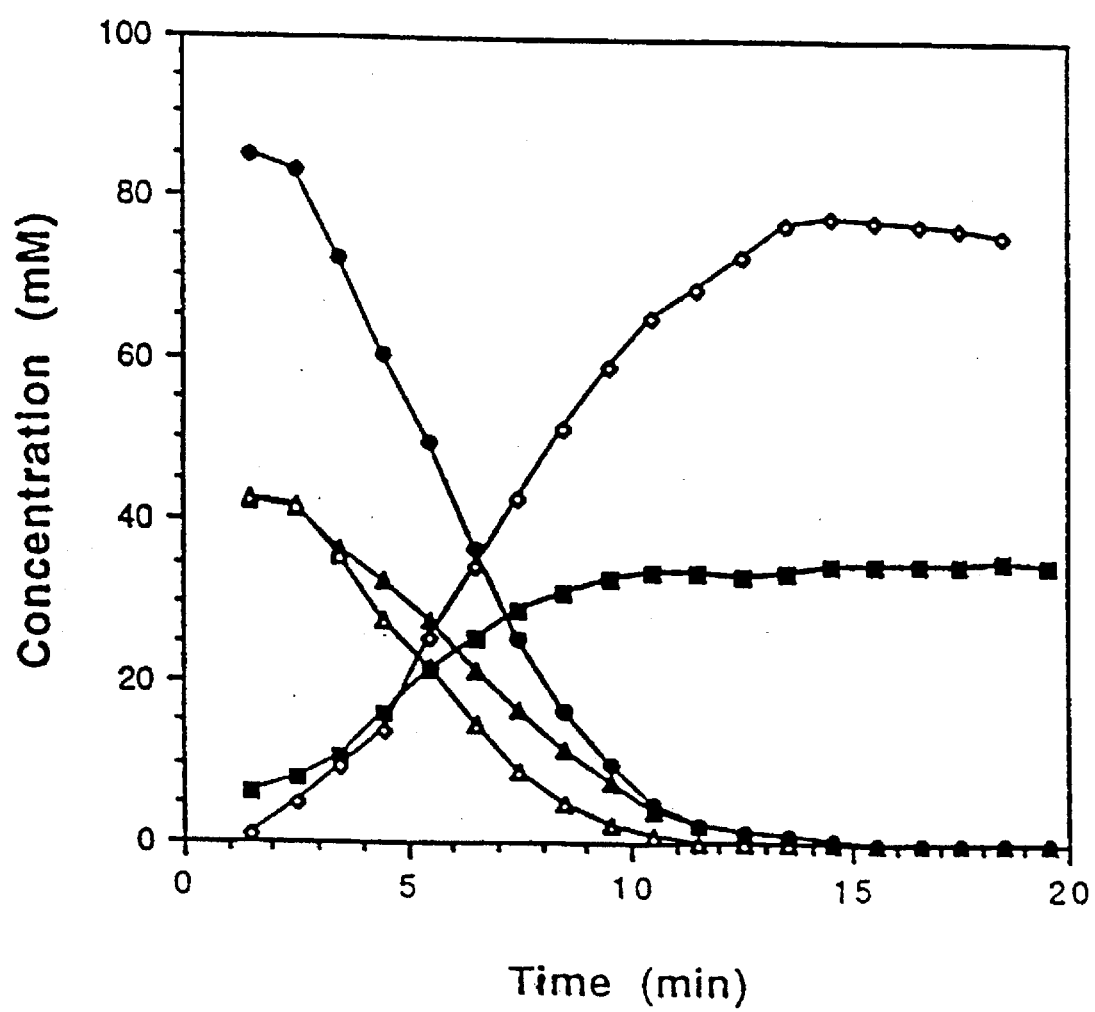

To determine the effect of the hog1-Δ1 mutation on the production of glycerol and ethanol during yeast formation, we used NMR spectroscopy to follow the metabolic conversion of [1-$^{13}$C]-glucose to [1-$^{13}$C]-glycerol and [2-$^{13}$C]-ethanol. The time course of changes in the concentrations of glucose, ethanol, and glycerol in the NMR tube are shown for the wild-type strain YPH499 in either control media (FIG. 7A) or in media containing 400 mM NaCl (FIG. 7B). The final concentrations of ethanol and glycerol were taken from their plateau levels at the end of the time course. For all strains, these concentrations were the same as those measured outside the cells after removal of the cells by centrifugation.

Deletion-disruption of HOG1 causes a decrease in total glycerol biosynthesis during fermentation with minimal effects on ethanol production (Table II and FIG. 8). Yeast production of glycerol and ethanol during fermentation of glucose was quantitated by in vivo $^{13}$C NMR spectroscopy. Cells from log-phase yeast cultures in YEPD media were washed in buffer and resuspended as a 35.5% solution in a 15 mm diameter NMR tube. $^{13}$C glucose was added to a final concentration of 85 mM. Spectra were taken every minute. Peaks in the NMR spectra corresponding to glycerol and ethanol were identified using standards. The area under each of these peaks was determined by integration, corrected for a saturation factor, and used to calculate the concentration of glycerol or ethanol in the NMR tube. In FIG. 7, the time course of changes in the concentrations of glucose, ethanol, and glycerol in the NMR tube are shown for the congenic wild type strain YPH499 in control and high osmolarity media. Final concentrations of ethanol and glycerol outside the cells (after removal of the cells by centrifugation) at the end of the experiment was the same as the final equilibrium values shown in FIG. 7. Table II shows the levels of ethanol and glycerol at the end of the fermentation for both strains. The final level of glycerol produced by the deletion-disruption mutant hog1-Δ1 is significantly lower than that of the wild-type strain. Note that the final level of ethanol produced is similar for wild-type and hog1-Δ1, resulting in a significant increase in the ratio of ethanol to glycerol in the fermentation product by the hog1-Δ1 mutant (FIG. 9).

EXAMPLE 7

A genomic clone on the plasmid pMM1 which complemented both the Osm$^s$ and the decreased glycerol response of hog2-1 contained an 11 kb insert; the restriction map of which is shown in FIG. 4. To further delineate the HOG2 gene, fragments of the genomic insert were subcloned into centromere vectors and tested for complementation of the Osm$^s$ phenotype of the hog2-1 mutant. Using this approach, HOG2 was localized to a 3 kb Sal I-Bgl II fragment. Southern blot hybridization of HOG2 to electrophoretically-separated *Saccharomyces cerevisiae* chromosomes showed that HOG2 is on chromosome IV. The DNA sequence of HOG2 was determined (FIG. 10), revealing a large open reading frame, 2.7 kb long, with a predicted protein of 896 amino acids with a molecular weight of 100 kDa. Northern hybridization using the cloned HOG2 gene as probe hybridized to a ~3.3 kb transcript, showing that HOG2 is expressed in vivo.

A deletion-disruption mutant of HOG2 was constructed by one-step genomic sequence replacement (Rothstein, *Meth. Enzym.* 101:228 (1989)) in which a 0.5 kb restriction fragment of HOG2 was deleted in vitro and replaced with the selectable marker URA3. A 3.9 kb Cla I-Xba I fragment from pMM1 containing part of HOG2 was inserted into pGEM-7Zf$^+$ (Promega). A 0.5 kb EcoR I-Sal I internal fragment of the hog2-complementing DNA was excised and replaced with a 1.8 kb EcoR I-Sal I fragment from YEp24 (Carlson and Botstein, 1982) containing the URA3 marker. The URA3-marked deletion mutation of HOG2 was excised from the plasmid by a Sac I-Hpa I cut and used to disrupt one copy of HOG2 in YPH501. The transformed Ura$^+$ diploids were sporulated, tetrads microdissected, and the growth properties of the haploid progeny tested on synthetic complete media lacking uracil or on rich media (YEPD) containing 0.9M NaCl to test for an Osm$^s$ phenotype. All complete tetrads segregated as 2 Ura$^+$20 Osm$^s$:2 Ura$^-$Osm$^R$. Southern blot analysis of the Ura$^+$ disrupted strain and YPH501 using the HOG2 gene as the probe confirmed the deletion-disruption of HOG2 in the hog2-Δ1 mutant strain. The segment of DNA deleted in hog2-Δ1 is within the protein coding region of HOG2 and includes DNA flanking PPH3 at its 5' end (Accession number X58858). Deletion mutations of this region of the yeast genome have not been previously reported. The Osm$^s$, reduced glycerol biosynthesis, and defective sporulation phenotypes of the hog2-Δ1 and hog2-1 mutants are almost indistinguishable.

Figure 6:
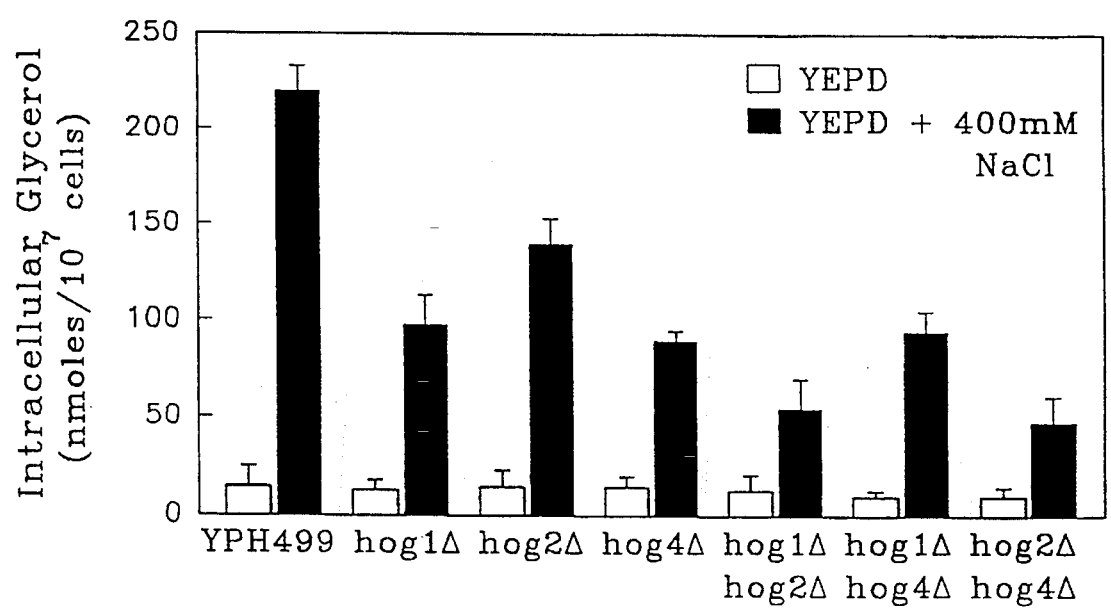
FIG. 6. Deletion-disruption mutations in the HOG genes cause a reduction in intracellular glycerol levels. hog1 Δ=hog1-Δ1, hog2 Δ=hog2-Δ1, and hog4 Δ=hog4-Δ1. Intracellular glycerol levels following a 1 hr incubation of cells in either YEPD or YEPD+0.4M NaCl.
Figure 8B:
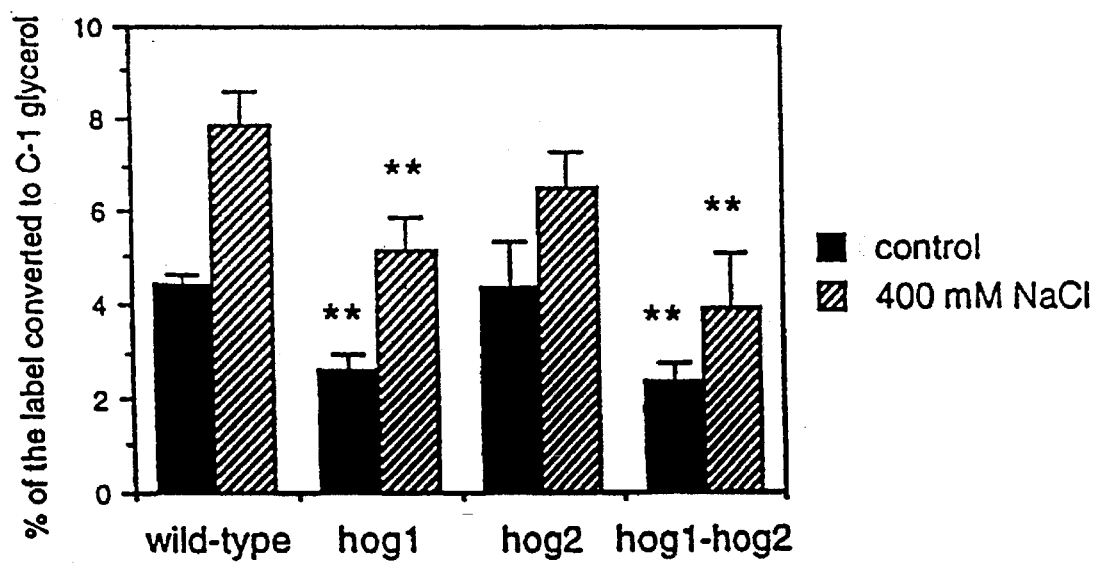

The deletion-disruption mutant hog2-Δ1 contained less intracellular glycerol than the congenic wild-type control strain YPH499 (FIG. 6). The final level of total glycerol produced by the hog2-Δ1 strain is lower than that of the wild-type strain in high osmolarity media (FIG. 8B and Table II). Deletion-disruption of HOG2 results in a significant increase in the final concentration and yield of ethanol (FIG. 8A and Table II) measured at the end of a yeast fermentation in control media. When fermentation was carried out in 400 mM NaCl media, the yield of ethanol increases to a high level for all strains, making it difficult to distinguish differences in ethanol yield between strains.

EXAMPLE 8

A genomic clone pJB4 which complemented the Osm$^s$ phenotype and decreased glycerol production of hog4-1 contained a 6.5 kb insert. To test whether HOG4 had been cloned, the chromosomal locus corresponding to the cloned DNA was marked with a selectable marker and shown to be tightly linked to the corresponding mutation. The restriction map of the original hog4-1-complementing clone is shown in FIG. 3. To further delineate the HOG4 gene, fragments of the genomic insert were subcloned into centromere vectors and tested for complementation of the Osm$^s$ phenotype of the hog4-1 mutant. Using this approach, HOG4 was localized to a 3.7 kb Kpn I-Spe I fragment (FIG. 4). HOG4 was identified as the previously cloned PBS2, a gene which confers resistance to the antibiotic polymyxin B when the gene is over-expressed (Boguslawaski, and Polazzi, Proc. Nat. Acad. Sci. USA 84:5848 (1987)). This identification is based on the following observations. First, when PBS2 is disrupted, the resulting strain is Osm$^s$ and has a terminal cell morphology in high osmolarity media that was indistinguishable from that of hog4-Δ1. Second, Southern blot hybridization of HOG4 to electrophoretically-separated Saccharomyces cerevisiae chromosomes showed HOG4 is on chromosome X, the same as PBS2. Third, PBS2 has a restriction map identical to that of HOG4, and, fourth, PBS2 complements the Osm$^s$ of a hog4-1 mutant when carried on a centromere plasmid.

The following procedure was used to disrupt hog4. A 5.5 kb fragment of hog4-1-complementing genomic DNA from an Spe I site in the genomic DNA to a Sal I site 150 bp off the insert and into vector sequence of pJB4 was inserted into pRS316. This plasmid, pJB4A, was cut with Hind III, relegated to remove 2.9 kb of hog4-complementing DNA, and the 1.2 kb Hind III-Hind III fragment from YEp24 containing URA3 inserted into this site. This deletion of HOG4 removed 1.8 kb of a 2 kb-long coding region plus 1.1 kb of adjacent 3'-noncoding region. The 3.8 kb Sal I-Spe I fragment containing the deleted/URA3-disrupted genomic DNA was ligated into the TRP1 plasmid pRS4 14 (Sikorski, R.S., and Hieter, P., Genetics 122:19 (1989)), to form pJB4D. A Sac I-Spe I fragment containing 1.5 and 0.5 kb of genomic DNA flanking the URA3 marker was used to transform YPH501. Ura$^+$ transformants were sporulated, tetrads dissected and tested for growth properties, glycerol accumulation. Co-segregation of Osm$^s$ and Ura$^+$ was seen in all tetrads analyzed. The Osm$^s$ of the hog4-Δ1 was complemented by the cloned HOG4 on pJB4D. Southern analysis of the disrupted strain and YPH501 confirmed the integration of the construction at the chromosomal locus of the cloned HOG4 DNA.

Boguslawaski, G., and Polazzi, T., Proc. Nat. Acad. Sci. USA 84:5848 (1987) described both the DNA sequence of PBS2/HOG4 and a procedure for making a deletion/disruption mutation in this gene. However, the process for using a HOG4 deletion/disruption mutation to lower glycerol production has not been available nor has the function of HOG4/PBS2, in regulating glycerol biosynthesis been previously recognized.

The deletion-disruption mutant hog4-Δ1 contained less intracellular glycerol than the congenic wild-type control strain YPH499 (FIG. 6). The accumulation of extracellular glycerol in the extracellular media in cells fermenting glucose was measured. Under identical conditions (500 mM glucose in synthetic complete media, 2hrs at 30° C.), wild-type (YPH499) produced 3.3±0.3 μmoles/10$^8$ cells while the hog4-Δ1 mutant produced 0.7±0.1 μmoles/10$^8$ cells.

EXAMPLE 9

A hog1-Δ1, hog2-Δ1 double mutant was constructed by genetic cross. A haploid hog1-Δ1::TRP1 ura3 trpl strain (described in Example 6) was mated to a haploid hog2-Δ1::URA3 ura3 trpl strain-(described in Example 7) and the resulting diploids sporulated. Tetrad asci were microdissected and individual spores micromanipulated to different positions on a YEPD plate. The double mutant appeared as a Ura$^+$ Trp$^+$ colony arising from the growth of a single spore.

The strain containing two deletion-disruption mutations, hog1-Δ1 and hog2-Δ1, had a level of intracellular glycerol not only lower than the congenic wild-type control strain YPH499 but lower than that induced by either of the single deletion-disruption mutations (FIG. 6). The total glycerol biosynthesis measured in cultures fermenting $^{13}$C glucose was lower for the double mutant than either single mutant (Table II).

The hog1-Δ1 and hog2-Δ1 double mutation significantly increases the ratio of ethanol to glycerol in the fermentation production (FIG. 9) without lowering ethanol yield (FIG. 8A) in both the control and 400 mM NaCl fermentation conditions. The hog1-Δ1 and hog2-Δ1 mutations had additive effects in reducing glycerol yield in NaCl media (Table III), demonstrating the utility of the double mutant approach for reducing glycerol production.

While not being bound by any theoretical model, one explanation for the incomplete block of glycerol biosynthesis in the hog Δ mutants is that accumulation of glycerol involves two or more pathways, each operating in parallel and requiring a different set of genes. The concentration of intracellular glycerol achieved in osmotically-stressed cells is therefore a summation of two or more independently controlled metabolic responses. Mutations in hog genes required for two different pathways would have additive or synergistic effects on osmotic stress-induced glycerol accumulation. This was observed in the hog1-Δ1, hog2-Δ1 and hog2-Δ1, hog4-Δ1 double mutants (FIG. 6). hog1-Δ1 and hog4-Δ1 had non-additive effects on osmotic-sensitive glycerol accumulation and growth, suggesting that HOG1 and HOG4 are necessary for the same pathway leading to glycerol accumulation in yeast cells.

Table II. Deletion-disruption mutations in the HOG genes causes a reduction in the final concentration of glycerol or an increase in the final concentration of ethanol in yeast fermentations. In vivo $^{13}$C nuclear magnetic resonance (NMR) spectroscopy was used to measure the concentration of

[2-$^{13}$C]-ethanol and [1-$^{13}$C]-glycerol (the major organic endproducts of fermentation), generated from the fermentation of [1-$^{13}$C] glucose, added to an initial concentration of 85 mM. See the legend to FIG. 7 for experimental details. Strains used in the fermentations are abbreviated as follows: wild-type, YPH499; hog1Δ, JBY10 containing the hog1-Δ1 mutation; hog2 Δ, JBY20 containing hog2-Δ1; hog1Δhog2 Δ, JBY 12 containing hog1-Δ1 and hog2-Δ1. Two conditions, with and without 400 mM NaCl, were used to assay fermentation (see text for explanation). Values for each strain and condition are the mean±st. dev. for data from three separate experiments. Values marked with ** are significantly different ($p<0.05$, Student's t-test) from those of the wild type strain assayed under the same conditions.

TABLE II

| | STRAIN | | | |
|---|---|---|---|---|
| PARA-METER | Wild-type | hog1 Δ | hog2 Δ | hog1 Δhog2 Δ |
| Ethanol (mM) | Control 45.1 (±4.2) | Control 54.5 (±9.4) | Control 59.6** (±4.1) | Control 49.1 (±5.8) |
| | Na 70.8 (±7.1) | Na 71.0 (±6.5) | Na 73.5 (±6.3) | Na 76.4 (±0.8) |
| Glycerol (mM) | Control 3.8 (±0.2) | Control 2.4** (±0.3) | Control 3.8 (±0.8) | Control 2.0** (±0.4) |
| | Na 6.7 | Na 4.4** | Na 5.5 | Na 3.3** |

TABLE II-continued

| | STRAIN | | | |
|---|---|---|---|---|
| PARA-METER | Wild-type | hog1 Δ | hog2 Δ | hog1 Δhog2 Δ |
| | (±0.6) | (±0.6) | (±0.7) | (±1.0) |

TABLE III

Additive effects of the hog1-Δ1 and hog2-Δ1 mutations on glycerol yield from yeast fermentation.

| Decrease in glycerol yield | Observed | | | Predicted |
|---|---|---|---|---|
| | hog1 | hog2 | hog1hog2 | hog1hog2 |
| Control media | −1.8% | −0% | −2.0% | −1.8% |
| 400 mM NaCl media | −2.7% | −1.3% | −3.9% | −4.0% |

Many other variations and modifications may be made in the materials, methods, and techniques described above by those having experience in this technology, without departing from the concepts of the present invention. Accordingly, it should be clearly understood that the materials, methods, and techniques referred to in the foregoing description are illustrative only and are not intended as limitations on the scope of this invention.

Other aspects, objects, and advantages of this invention can be obtained from a study of the disclosure and appended claims.

I claim:

1. A biologically pure culture of a mutated microorganism of the genus Saccharomyces or Torulaspora comprising: A deletion disruption mutated microorganism produced by alteration of a gene DNA sequence selected from the group consisting of HOG1, HOG2 and HOG4.

2. A culture according to claim 1 wherein the microorganism is a strain of *Saccharomyces cerevisiae* Hansen.

3. A culture according to claim 1 wherein the microorganism comprises *Saccharomyces cerevisiae* S288C.

4. A culture according to claim 1 in which the fermentation product has less than 60% of the amount of glycerol produced by the non-mutated parental strain.

5. A culture according to claim 1 in which the fermentation product has less than 50% of the amount of glycerol produced by the non-mutated parental strain.

6. A microorganism that is transformed with recombinant vector comprising a DNA segment selected from the group consisting of the HOG1 gene, the HOG2 gene and the HOG4 gene.

7. A microorganism according to claim 6 transformed by a recombinant vector having multiple copies of a HOG gene.

8. A microorganism according to claim 6 transformed by a recombinant vector having a strong promoter DNA sequence 5' to the HOG DNA segment.

9. A microorganism according to claim 6 comprising the sequence of SEQ ID NO: 1.

10. A microorganism according to claim 6 comprising the sequence of SEQ ID NO: 2.

11. A microorganism according to claim 6 in which the microorganism is *Saccharomyces* cerevisiae Hansen.

12. A transformed microorganism according to claim 6, in which the microorganism is *Saccharomyces cerevisiae* S288C.

13. A microorganism of culture deposit NRRL 18826 of the Agricultural Research Culture Collection.

14. A microorganism of culture deposit NRRL 18827 of the Agricultural Research Culture Collection.

15. A microorganism of culture deposit NRRL 18828 of the Agricultural Research Culture Collection.

16. A microorganism transformed by insertion of a mutated DNA segment having at least one sequence selected from the group consisting of the HOG1 gene, the HOG2 gene, the HOG4 gene and combinations thereof.

17. A microorganism of claim 16 in which the mutated DNA segment is homologous to the HOG2 gene.

18. A microorganism of claim 16 in which the mutated DNA segment is the HOG1 gene.

19. An isolated and purified DNA segment complementing a low intracellular glycerol producing mutant which converts an osmolarity sensitive yeast cell to an osmolarity resistant strain when the DNA segment is inserted into the yeast cell, wherein the mutant is of a gene selected from the group consisting of HOG1 and HOG2 or HOG4.

20. A DNA segment according to claim 19 in which the gene is HOG1.

21. A DNA segment according to claim 20 having two ends and a Sau 3A/BamH I restriction endonuclease cleavage site at one of the ends.

22. The DNA segment according to claim 21 having an EcoR I restriction endonuclease cleavage site at the end opposite the Sau 3A/BamH I cleavage site.

23. The DNA segment according to claim 22 further characterized by comprising about 2.1 kilobases.

24. The DNA segment according to claim 19 in which the gene is HOG2.

25. A recombinant vector which comprises a DNA segment of claim 19.

26. The recombinant vector of claim 25 which further comprises a gene expression promoter DNA sequence.

27. A transformed yeast cell having a DNA segment of claim 19 inserted in a manner such that the transformed cell expresses the inserted DNA.

28. A transformed cell according to claim 27 which produces more glycerol than the untransformed parental strain.

29. A transformed yeast cell which produces less glycerol than the untransformed cell due to the insertion of an in vitro mutated DNA segment selected from the group consisting of the DNA segment having the sequence of SEQ ID NO: 1 or the DNA segment having the sequence of SEQ ID NO: 2.

30. An isolated and purified DNA segment having at least one sequence selected from the group consisting of the sequence of SEQ ID NO: 1 and a sequence similar to the sequence of SEQ ID NO: 1 that encodes the same protein as the sequence of SEQ ID NO: 1.

31. An isolated and purified DNA segment having the sequence of SEQ ID NO: 1.

32. An isolated and purified DNA segment having the sequence of SEQ ID NO: 1 and a sequence coding for a selectable marker, wherein the selectable marker is TRP1.

33. An isolated and purified DNA fragment having at least one sequence selected from the group consisting of the sequence of SEQ ID NO: 2 and a sequence similar to the sequence of SEQ ID NO: 2 that encodes the same protein as the sequence of SEQ ID NO: 2.

34. An isolated and purified DNA fragment having the sequence of SEQ ID NO: 2.

35. An isolated and purified DNA segment having the sequence of SEQ ID NO: 2 and a sequence coding for a selectable marker, wherein the selectable marker is URA3.

* * * * *

UNITED STATES PATENT AND TRADEMARK OFFICE
CERTIFICATE OF CORRECTION

PATENT NO. : 5,545,556
DATED : August 13, 1996
INVENTOR(S) : Gustin

It is certified that error appears in the above-indentified patent and that said Letters Patent is hereby corrected as shown below:

Column 2, line 41, "Osmolarity" should read -- Osmolality--.

Column 5, line 20, " (also called hog1-1 and hog24)" should read -- (also called hog1-1 and hog2-1)--.

Column 5, line 24, "HOG 1" should read -- HOG1--.

Column 5, line 36, "YEPD Or" should read -- YEPD or--.

Column 5, line 60, "NaCl YEPD" should read -- NaCl-YEPD--.

Column 6, line 21, "(MATa/MATatrp1/trp1" should read --(MATa/MATαtrpl/trp 1--.

Column 15, line 41, "AND$^+$" should read --NAD$^+$--.

Column 17, line 47, "disrupt hog4" should read -- disrupt HOG4--.

Column 18, line 54, "in hog genes" should read -- in HOG genes--.

Signed and Sealed this

Seventeenth Day of December, 1996

Attest:

BRUCE LEHMAN

*Attesting Officer*  *Commissioner of Patents and Trademarks*